United States Patent
Paczal et al.

(10) Patent No.: US 10,457,689 B2
(45) Date of Patent: Oct. 29, 2019

(54) AMMONIUM DERIVATIVES, A PROCESS FOR THEIR PREPARATION AND PHARMACEUTICAL COMPOSITIONS CONTAINING THEM

(71) Applicants: LES LABORATOIRES SERVIER, Suresnes (FR); VERNALIS (R&D) LTD, Winnersh (GB)

(72) Inventors: Attila Paczal, Budapest (HU); Zoltán Szlávik, Budapest (HU); András Kotschy, Törökbálint (HU); Maïa Chanrion, Issy les Moulineaux (FR); Ana Leticia Maragno, Croissy-sur-Seine (FR); Olivier Geneste, Rueil-Malmaison (FR); Didier Demarles, Checy (FR); Balázs Bálint, Fót (HU); Szabolcs Sipos, Budapest (HU)

(73) Assignees: LES LABORATOIRES SERVIER, Suresnes (FR); VERNALIS (R&D) LTD, Winnersh Berkshire (GB)

( * ) Notice: Subject to any disclaimer, the term of this patent is extended or adjusted under 35 U.S.C. 154(b) by 0 days.

(21) Appl. No.: 16/069,891

(22) PCT Filed: Dec. 19, 2016

(86) PCT No.: PCT/EP2016/081688
§ 371 (c)(1),
(2) Date: Jul. 13, 2018

(87) PCT Pub. No.: WO2017/125224
PCT Pub. Date: Jul. 27, 2017

(65) Prior Publication Data
US 2019/0031677 A1 Jan. 31, 2019

(30) Foreign Application Priority Data
Jan. 19, 2016 (FR) ...................... 16 50411

(51) Int. Cl.
C07D 495/04 (2006.01)
A61K 31/519 (2006.01)
C07F 9/6561 (2006.01)
A61P 35/02 (2006.01)
A61K 45/06 (2006.01)

(52) U.S. Cl.
CPC ............ *C07D 495/04* (2013.01); *A61K 45/06* (2013.01); *A61P 35/02* (2018.01); *C07F 9/6561* (2013.01); *A61K 2300/00* (2013.01)

(58) Field of Classification Search
None
See application file for complete search history.

(56) References Cited

FOREIGN PATENT DOCUMENTS

EP    2886545    6/2015

OTHER PUBLICATIONS

International Search Report and Written Opinion for PCT/EP2016/081688 dated Jan. 18, 2017.

*Primary Examiner* — Samantha L Shterengarts
(74) *Attorney, Agent, or Firm* — Hueschen and Sage

(57) ABSTRACT

Compounds of formula (I):

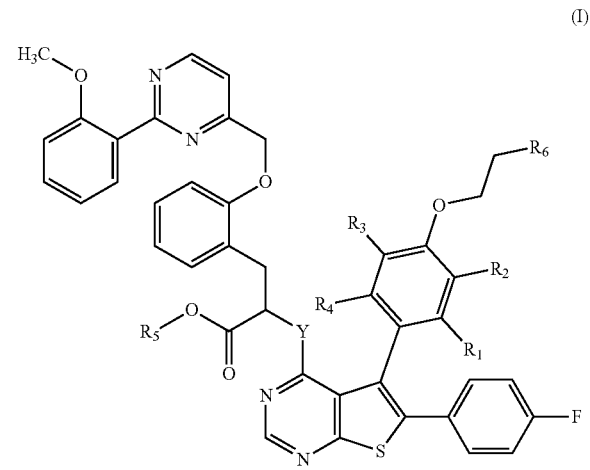

wherein $R_1$, $R_2$, $R_3$, $R_4$, $R_5$, $R_6$ and Y are as defined in the description.
Medicaments.

24 Claims, No Drawings

AMMONIUM DERIVATIVES, A PROCESS FOR THEIR PREPARATION AND PHARMACEUTICAL COMPOSITIONS CONTAINING THEM

The present invention relates to new ammonium derivatives, to a process for their preparation and to pharmaceutical compositions containing them.

The compounds of the present invention are new and have very valuable pharmacological characteristics in the field of apoptosis and oncology.

Apoptosis, or programmed cell death, is a physiological process that is crucial for embryonic development and maintenance of tissue homeostasis.

Apoptotic-type cell death involves morphological changes such as condensation of the nucleus, DNA fragmentation and also biochemical phenomena such as the activation of caspases which cause damage to key structural components of the cell, so inducing its disassembly and death. Regulation of the process of apoptosis is complex and involves the activation or repression of several intracellular signalling pathways (Cory et al. *Nature Review Cancer* 2002, 2, 647-650).

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in auto-immune diseases, inflammatory diseases and viral infections. Accordingly, absence of apoptosis is one of the phenotypic signatures of cancer (Hanahan et al. *Cell* 2000, 100, 57-70).

The anti-apoptotic proteins of the Bcl-2 family are associated with numerous pathologies. The involvement of proteins of the Bcl-2 family is described in numerous types of cancer, such as colon cancer, breast cancer, small-cell lung cancer, non-small-cell lung cancer, bladder cancer, ovarian cancer, prostate cancer, chronic lymphoid leukaemia, lymphoma, myeloma, acute myeloid leukemia, pancreatic cancer, etc. Overexpression of the anti-apoptotic proteins of the Bcl-2 family is involved in tumorigenesis, in resistance to chemotherapy and in the clinical prognosis of patients affected by cancer. Notably, Mcl-1, an, anti-apoptotic Bcl-2 family member, is overexpressed in various types of cancer (Beroukhim et. al. *Nature* 2010, 899-905). There is, therefore, a therapeutic need for compounds that inhibit the anti-apoptotic activity of the proteins of the Bcl-2 family.

Recently, thienopyrimidine derivatives have been described as potent Mcl-1 inhibitors useful for the treatment of cancers (WO 20151097123).

The present invention provides novel ammonium derivatives that have, pro-apoptotic properties making it possible to use them in pathologies involving a defect in apoptosis, such as, for example, in the treatment of cancer and of immune and auto-immune diseases. Moreover, the compounds of the present invention have high solubility as well as remarkable and unexpected pharmacological effects which could lead to very interesting candidates for oncology.

The present invention relates more especially to compounds of formula (I):

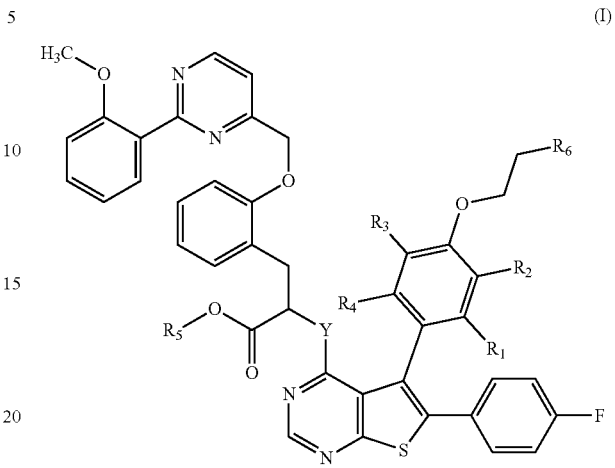

wherein:
Y represents a —NH— group or an oxygen atom,
$R_1$ represents a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)alkoxy group, a —S—($C_1$-$C_6$)alkyl group, a linear or branched ($C_1$-$C_6$)polyhaloalkyl group, a hydroxy group, a hydroxy($C_1$-$C_6$)alkyl group, a cyano group, —$NR_9R_9'$, —$Cy_1$ or a halogen atom,
$R_2$, $R_3$ and $R_4$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, a —S—($C_1$-$C_6$)alkyl group, a cyano group, a nitro group, -alkyl($C_0$-$C_6$)—$NR_9R_9'$, —O-alkyl($C_1$-$C_6$)—$NR_9R_9'$, —C(O)—$OR_9'$, —O—C(O)—$R_9$, —C(O)—$NR_9R_9'$, —$NR_9$—C(O)—$R_9'$, —$NR_9$—C(O)—$OR_9'$, -alkyl($C_1$-$C_6$)—$NR_9$—C(O)—$R_9'$, —$SO_2$—$NR_9R_9'$, —$SO_2$-alkyl($C_1$-$C_6$),
$R_5$ represents a hydrogen atom,
$R_6$ represents the group

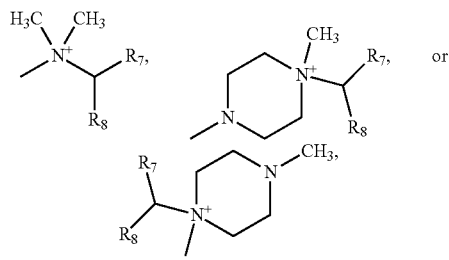

$R_7$ represents a hydrogen atom or a linear or branched ($C_1$-$C_6$)alkyl group,
$R_8$ represents a —O—P(O)($O^-$)($O^-$) group, a —O—P(O)(O)($OR_{10}$) group, a —O—P(O)($OR_{10}$)($OR_{10}'$) group, a —O—$SO_2$—$O^-$ group, a —O—$SO_2$—$OR_{10}$ group, —$Cy_2$, a —O—C(O)—$R_9$ group, a —O—C(O)—$OR_9$ group or a —O—C(O)—$NR_9R_9'$ group;

R₉ and R₉' independently of one another represent a hydrogen atom, a linear or branched $(C_1-C_6)$alkyl group or a linear or branched amino$(C_1-C_6)$alkyl group, R₁₀ and R₁₀' independently of one another represent a hydrogen atom, a linear or branched $(C_1-C_6)$alkyl group or an arylalkyl$(C_1-C_6)$ group, Cy₁ and Cy₂ independently of one another, represent a cycloalkyl group, a heterocycloalkyl group, an aryl group or a heteroaryl group, it being possible for the ammonium so defined to exist as a zwitterionic form or to have a monovalent anionic counterion, it being understood that
- "aryl" means a phenyl or naphthyl group,
- "heteroaryl" means any mono- or bi-cyclic group composed of from 5 to 10 ring members, having at least one aromatic moiety and containing from 1 to 3 heteroatoms selected from oxygen, sulphur and nitrogen,
- "cycloalkyl" means any mono- or bi-cyclic non-aromatic carbocyclic group containing from 3 to 10 ring members,
- "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, it being possible for the aryl, heteroaryl, cycloalkyl and heterocycloalkyl groups so defined, and the alkyl, alkenyl, alkynyl, alkoxy groups, to be substituted by from 1 to 4 groups selected from linear or branched $(C_1-C_6)$alkyl, linear or branched $(C_2-C_6)$alkenyl group, linear or branched $(C_2-C_6)$alkynyl group, linear or branched $(C_1-C_6)$alkoxy, $(C_1-C_6)$alkyl-S—, hydroxy, oxo (or N-oxide where appropriate), nitro, cyano, —C(O)—OR', —O—C(O)—R', —C(O)—NR'R", —NR'R", —(C=NR')—OR", linear or branched $(C_1-C_6)$polyhaloalkyl, trifluoromethoxy or halogen, it being understood that R' and R" independently of one another represent a hydrogen atom or a linear or branched $(C_1-C_6)$ alkyl group, their enantiomers, diastereoisomers and atropisomers, and addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Depending on their electronic charge, compounds of formula (I) can have a zwitterionic form which means a neutral molecule with a positive and a negative electrical charge. For compounds according to the invention, examples of a zwitterionic form can be as follows:

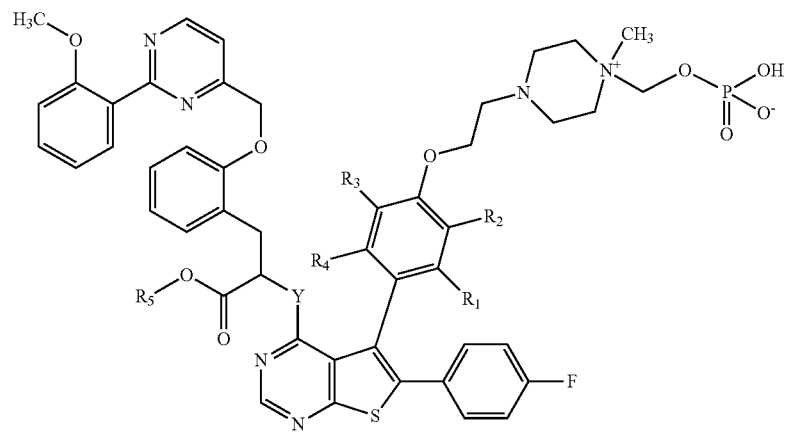

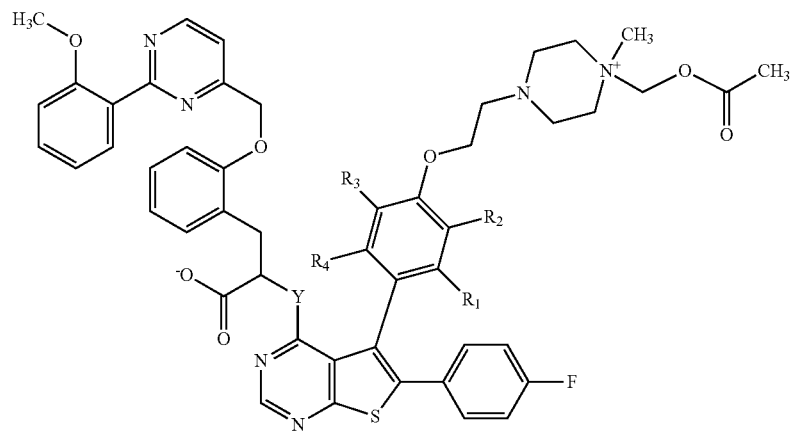

Depending on their electronic charge, compounds of formula (I) can contain one pharmaceutically acceptable monovalent anionic counterion $M_1^-$, which can be selected from bromide, chloride, iodide, acetate, trifluoroacetate, benzoate, mesylate, tosylate, triflate, or the like. For compounds according to the invention, an example can be as follows:

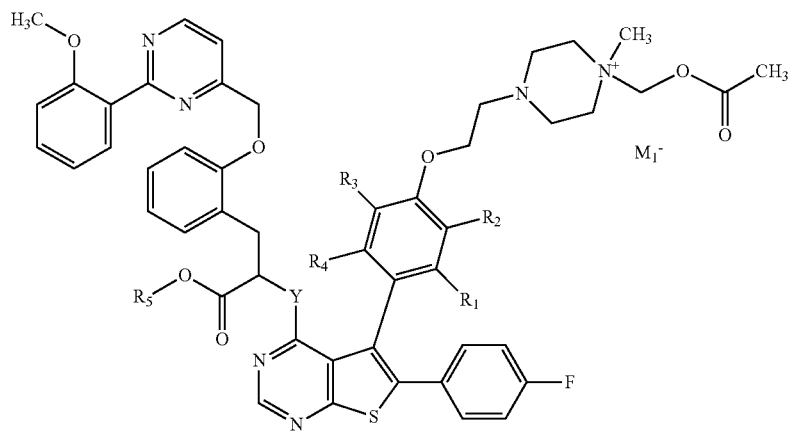

Depending on their electronic charge, compounds of formula (I) can contain one pharmaceutically acceptable monovalent cationic counterion $M_2^+$, which can be selected from sodium, potassium, lithium ammonium, aminoacid or the like. For compounds according to the invention, examples can be as follows:

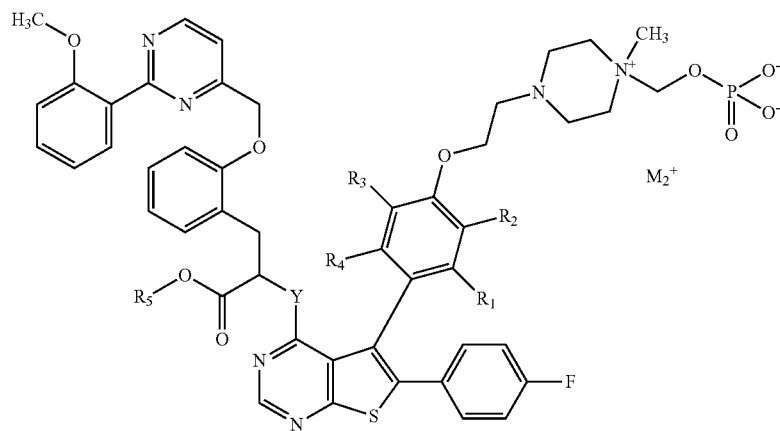

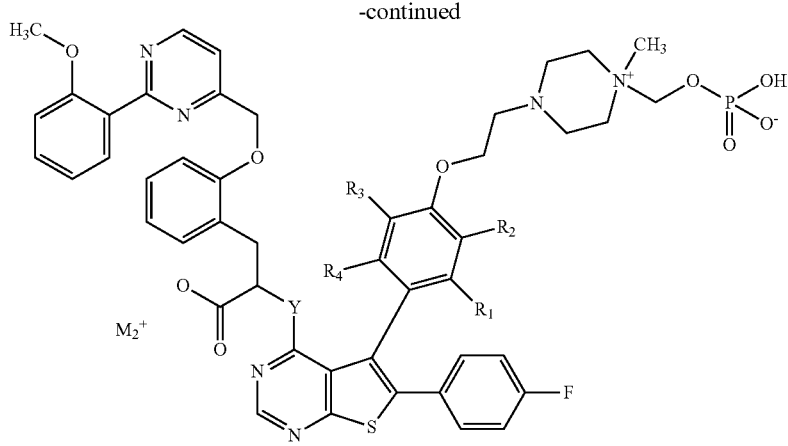

Depending on their electronic charge, compounds of formula (I) can contain one pharmaceutically acceptable divalent canonic counterion $M_3^{2+}$, which can be selected from calcium, magnesium, aluminium, aminoacid or the like, or two pharmaceutically acceptable monovalent cationic counterions $M_2^+$, identical or different. For compounds according to the invention, an example can be as follows:

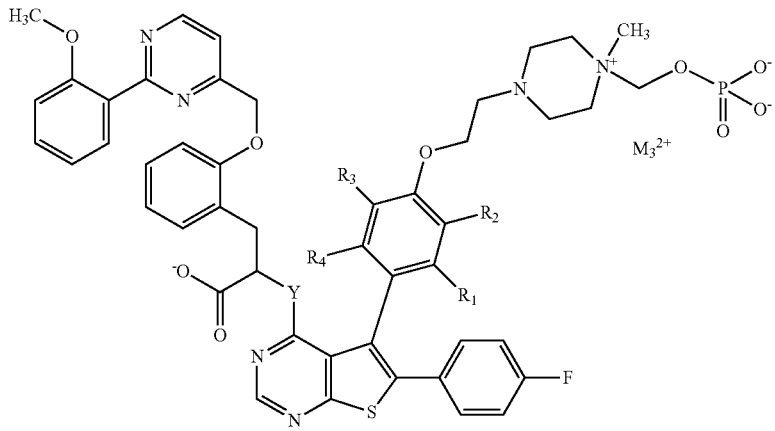

Y preferably represents an oxygen atom.

Advantageously, at least one of the groups selected from $R_2$, $R_3$ and $R_4$ does not represent a hydrogen atom.

In another embodiment of the invention, an advantageous possibility consists of compounds of formula (I-a):

(I-a)

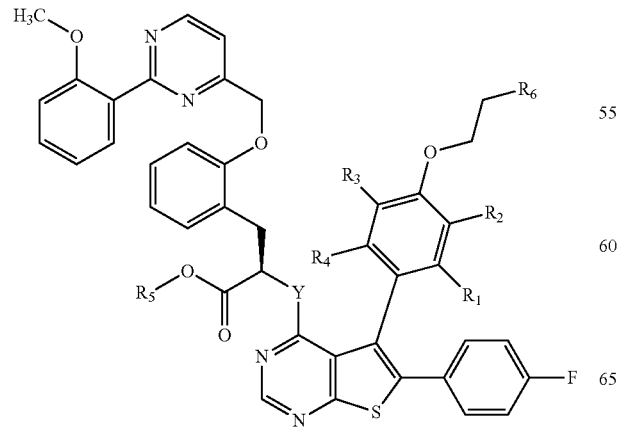

wherein $R_2$, $R_2$, $R_3$, $R_4$, $R_5$, $R_6$ and Y are as defined for formula (I).

In the preferred compounds of the invention, represents a linear or branched ($C_1$-$C_6$)alkyl group or a halogen atom. More preferably, $R_1$ represents a methyl group, an ethyl group, a chlorine atom or a bromine atom. Even more preferably, $R_1$ represents an ethyl group or a bromine atom. More particularly, $R_1$ represents a bromine atom. Advantageously, $R_1$ represents a methyl group.

Atropisomers are stereoisomers arising because of hindered rotation about a single bond, where energy differences due to steric strain or other contributors create a barrier to rotation that is high enough to allow for isolation of individual conformers (Bringmann, et al. *Angew. Chem. Int. Ed.* 2005, 44, 5384-5427). For compounds according to the invention atropisomers are as follows:

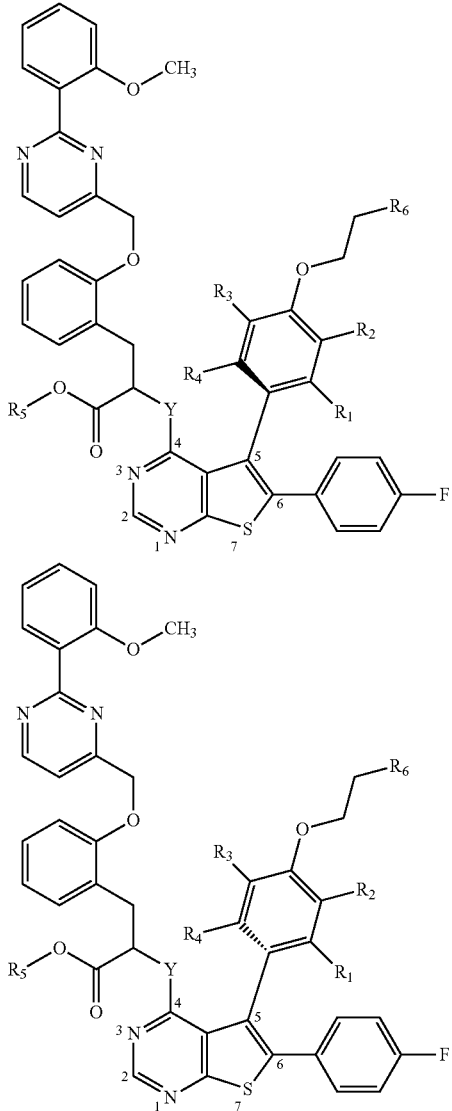

Preferred atropisomer is ($5S_a$).

Advantageously, $R_2$ represents a halogen atom, a hydroxy group, a linear or branched ($C_1$-$C_6$)alkoxy group. More preferably, $R_2$ represents a chlorine atom.

$R_3$ and $R_4$ preferably represent a hydrogen atom. In an advantageous embodiment, the substituents of the pair ($R_1$, $R_4$) are identical and the substituents of the pair ($R_2$, $R_3$) are identical. In the preferred compounds of the invention, the substituents of the pair ($R_1$, $R_4$) are identical and represent a ($C_1$-$C_6$)alkyl group, preferably a methyl group, whereas the substituents of the pair ($R_2$, $R_3$) are identical and represent a hydrogen atom or a halogen atom, preferably a chlorine atom.

Advantageously, represents the group

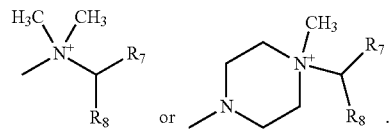

More preferably, $R_6$ represents the group

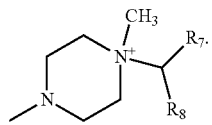

In the preferred compounds of the invention, $R_7$ represents a methyl group or a hydrogen atom. More preferably, $R_7$ represents a hydrogen atom.

Advantageous, $R_8$ represents a —O—P(O)(O$^-$)(OR$_{10}$) group in which $R_{10}$ preferentially represents a hydrogen atom, a benzyl group or a methyl group. In another preferred embodiment of the invention, $R_8$ represents a —O—SO$_2$—O$^-$ group. Preferably, $R_8$ represents a 5-methyl-2-oxo-1,3-dioxol-4-yl group; a —O—C(O)—CH$_3$ group; a —O—C(O)-tBu group; a —O—C(O)—CH$_2$—NH$_2$ group; a —O—C(O)—CH[CH(CH$_3$)$_2$]—NH$_2$ group; a —O—C(O)—O—CH$_2$CH$_3$ group; or a —O—C(O)—N(CH$_2$CH$_3$)$_2$ group. Even more preferably, $R_8$ represents a —O—P(O)(O$^-$)(OH) group.

Preferred compounds of the invention are:
{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl hydrogen phosphate;
benzyl {4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl phosphate;
{4-[2-(4-{(5S$_a$)-4-[(1R)-1-carboxy-2-(2-{[2-(2-methylphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl methyl phosphate;
{4-[2-(4-{(5S$_a$)-4-[(1R)-1-carboxy-2-(2-{[2-(2-methylphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl hydrogen phosphate;
{4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}methyl hydrogen phosphate;

benzyl {4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}methyl phosphate;

{4-[2-(3-bromo-4-{(5S$_a$)-4-[(1R)-1-carboxy-2-(2-{[2-(2-methoxyphenyl)pyrimidin-4-yl-]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}methyl methyl phosphate;

N-[(5S$_a$)-5-{3-chloro-4-[2-(4-{[(hydroxyphosphinato)oxy]methyl}-4-methylpiperazin-4-ium-1-yl)ethoxy]-2-methylphenyl}-6-(4-fluorophenyl)thieno[2,3-d]pyrimidin-4-yl]-2-{[2-(2-methoxyphenyl)pyrimidin-4-yl]methoxy}-D-phenylalanine;

{4-[2-(4-{(4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2,6-dichloro-3,5-dimethylphenoxy)ethyl]-1-methylpiperazin-1-ium-1-yl}methyl hydrogen phosphate;

{4-[2-(4-{4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-3,5-dimethylphenoxy)ethyl]-1-methylpiperazin-1-ium-1-yl}methyl hydrogen phosphate;

{[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl](dimethyl)ammonio}methyl hydrogen phosphate;

1-{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}ethyl hydrogen phosphate;

{4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}ethyl hydrogen phosphate;

{1-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-4-methylpiperazin-1-ium-1-yl}methyl hydrogen phosphate;

{1-[2-(3-bromo-4-{(5S$_a$)-4-[(1R)-1-carboxy-2-(2-{[2-(2-methoxyphenyl)pyrimidin-1-yl]methoxy}phenyl)ethoxy]-6-(4-fluorophenyl)thieno[2,3-d]pyrimidin-5-yl}-2-chlorophenoxy)ethyl]-4-methylpiperazin-1-ium-1-yl}methyl hydrogen phosphate;

{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}2-chloro-3-methylphenoxy)ethyl]-1-methylpiperazin-1-ium-1-yl}methyl phosphate;

1-[(acetyloxy)methyl]-4-[2-(4-{(5S$_a$)-4-[(1R)-1-carboxy-2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium;

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno)-[2,3-d]pyrimidin-5-yl}-2-chloro-3-methylphenoxy)ethyl]-1-{[(ethoxycarbonyl)oxy]methyl}-1-methylpiperazin-1-ium;

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno)-[2,3-d]pyrimidin-5-yl}-2-chloro-3-methylphenoxy)ethyl]-1-{[(diethylcarbamoyl)oxy]methyl}-1-methylpiperazin-1-ium;

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno)-[2,3-d]pyrimidin-5-yl}-2-chloro-3-methylphenoxy)ethyl]-1-[(glycyloxy)methyl]-1-methylpiperazin-1-ium;

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno)-[2,3-d]pyrimidin-5-yl}-2-chloro-3-methylphenoxy)ethyl]-1-{[(diethylcarbamoyl)oxy]methyl}-1-methylpiperazin-1-ium;

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno)-[2,3-d]pyrimidin-5-yl}-2-chloro-3-methylphenoxy)ethyl]-1-methyl-1-[(5-methyl-2-oxo-1,3-dioxol-4-yl)methyl]piperazin-1-ium;

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno)-[2,3-d]pyrimidin-5-yl}-2-chloro-3-methylphenoxy)ethyl]-1-methyl-1-[(L-valyloxy)methyl]piperazin-1-ium;

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno)-[2,3-d]pyrimidin-5-yl}-2-chloro-3-methylphenoxy)ethyl]-1-{[(2,2-dimethylpropanoyl)oxy]methyl}-1-methylpiperazin-1-ium;

1-[(acetyloxy)methyl]-4-[2-(2-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium;

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-{[(ethoxycarbonyl)oxy]methyl}-1-methylpiperazin-1-ium;

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-{[(diethylcarbamoyl)oxy]methyl}-1-methylpiperazin-1-ium;

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-[(glycyloxy)methyl]-1-methylpiperazin-1-ium;

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-{1-[(diethylcarbamoyl)oxy]ethyl}-1-methylpiperazin-1-ium;

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methyl-1-[(5-methyl-2-oxo-1,3-dioxol-4-yl)methyl]piperazin-1-ium;

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methyl-1-[(L-valyloxy)methyl]piperazin-1-ium;

4-[2-(3-bromo-4-{(5S$_a$)-4-[(1R)-1-carboxy-2-(2-{[2-(2-methoxyphenyl)pyrimidin-4-yl]methoxy}phenyl)

ethoxy]-6-(4-fluorophenyl)thieno[2,3-d]pyrimidin-5-yl}-2-chlorophenoxy)ethyl]-1-{[(2,2-dimethylpropanoyl)oxy]methyl}-1-methylpiperazin-1-ium.

Among the preferred compounds of the invention there may be mentioned:

{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl hydrogen phosphate;

benzyl {4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl phosphate;

{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl methyl phosphate;

{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl methyl phosphate;

{4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}methyl hydrogen phosphate;

benzyl {4-[2-(3-bromo-4-{(5S$_a$)-4-[(1R)-1-carboxy-2-(2-{[2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}methyl phosphate;

{4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}methyl methyl phosphate;

N-[(5S$_a$)-5-{3-chloro-4-[2-(4-{[(hydroxyphosphinato)oxy]methyl}-4-methylpiperazin-4-ium-1-yl)ethoxy]-2-methylphenyl}-6-(4-fluorophenyl)thieno[2,3-d]pyrimidin-4-yl]-2-{[2-(2-methoxyphenyl)pyrimidin-4-yl]methoxy}-D-phenylalanine;

{4-[2-(4-{4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2,6-dichloro-3,5-dimethylphenoxy)ethyl]-1-methylpiperazin-1-ium-1-yl}methyl hydrogen phosphate;

{4-[2-(4-{4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-3,5-dimethylphenoxy)ethyl]-1-methylpiperazin-1-ium-1-yl}methyl hydrogen phosphate;

{[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl](dimethyl)ammonio}methyl hydrogen phosphate;

{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}ethyl hydrogen phosphate;

1-{4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-yl}ethyl hydrogen phosphate;

{1-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-4-methylpiperazin-1-ium-1-yl}methyl hydrogen phosphate;

{1-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-4 methylpiperazin-1-ium-1-yl}methyl hydrogen phosphate, Preferred compounds of the invention are:

{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl hydrogen phosphate;

{4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}methyl hydrogen phosphate;

{[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl](dimethyl)ammonio}methyl hydrogen phosphate;

The invention relates also to a process for the preparation of compounds of formula (I), which process is characterised in that there is used as starting material the compound of formula (II):

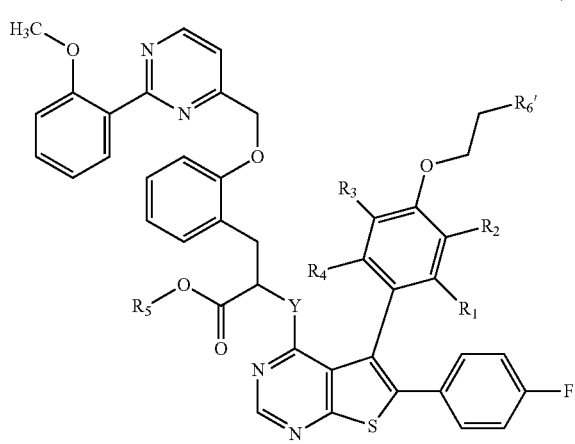

(II)

wherein $R_1$, $R_2$, $R_3$, $R_4$, $R_5$, and V are as defined for formula (I), and $R_6'$ represents a —N(CH$_3$)$_2$ group or a 4-methylpiperazinyl group, which is subjected to a reaction protecting the carboxylic acid function to yield the compound of formula (III):

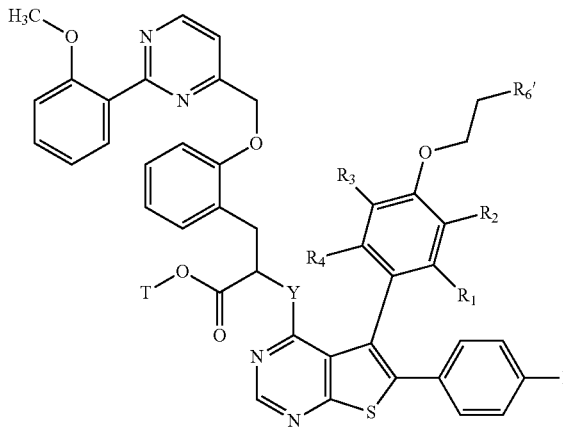

wherein $R_1$, $R_2$, $R_3$, $R_4$, $R_6'$ and V are as defined hereinbefore, and T represents a protecting group for the carboxylic acid function such as, for example,
a para-methoxybenzyl group,
which is subjected to coupling with a compound of formula (IV):

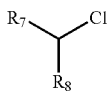

wherein $R_7$ and $R_8$ are as defined for formula (I),
to yield the of formula (V):

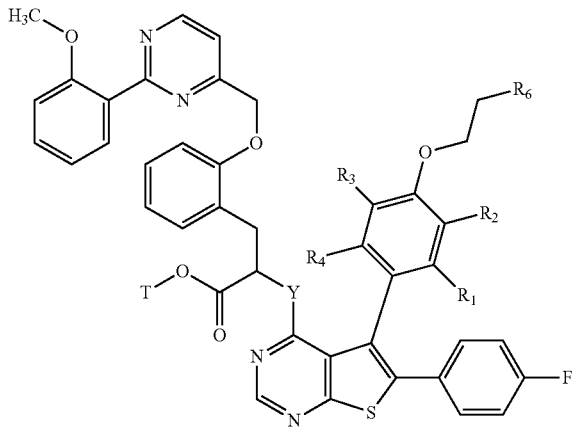

wherein $R_1$, $R_2$, $R_3$, $R_4$, T and Y are as defined hereinbefore, and $R_6$ is as defined in formula (I),
which is then subjected to a reaction deprotecting the carboxylic acid function,
to yield the compound of formula (I), which may be purified according to a conventional separation technique, which is converted, if desired, into its addition salts with a pharmaceutically acceptable acid or base and which is optionally separated into its isomers according to a conventional separation technique, it being understood that at any moment considered appropriate during the course of the process described above, some groups (hydroxy, amino . . . ) of the starting reagents or of the synthesis intermediates can be protected, subsequently deprotected and functionalized, as required by the synthesis.

The compounds of formulae (II) and (IV) are either commercially available or can be obtained by the person skilled in the art using conventional chemical reactions described in the literature.

Pharmacological study of the compounds of the invention has shown that they have pro-apoptotic properties. The ability to reactivate the apoptotic process in cancerous cells is of major therapeutic interest in the treatment of cancers and of immune and auto-immune diseases.

More especially, the compounds according to the invention will be useful in the treatment of chemo- or radio-resistant cancers.

Among the cancer treatments envisaged there may be mentioned, without implying any limitation, treatment of cancers of the bladder, brain, breast and uterus, chronic lymphoid leukaemias, cancer of the colon, œsophagus and liver, lymphoblastic leukaemias, acute myeloid leukaemias, lymphomas, melanomas, malignant haemopathies, myelomas, ovarian cancer, non-small-cell lung cancer, prostate cancer, pancreatic cancer and small-cell lung cancer.

The present invention relates also to pharmaceutical compositions comprising at least one compound of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the combination of a compound of formula (I) with an anticancer agent selected from genotoxic agents, mitotic poisons, anti-metabolites, proteasome inhibitors, kinase inhibitors and antibodies, and also to pharmaceutical compositions comprising that type of combination and their use in the manufacture of medicaments for use in the treatment of cancer.

Advantageously, the present invention relates to the combination of a compound of formula (I) with an EGFR inhibitor, and also to pharmaceutical compositions comprising that type of combination.

In another embodiment, the present invention relates to the combination of a compound of formula (I) with a mTOR/PI3K inhibitor, and also to pharmaceutical compositions comprising that type of combination.

In a preferred embodiment, the present invention relates to the combination of a compound of formula (I) with a MEK inhibitor, and also to pharmaceutical compositions comprising that type of combination.

Preferably, the present invention relates to the combination of a compound of formula (I) with a HER2 inhibitor, and also to pharmaceutical compositions comprising that type of combination.

Advantageously, the present invention relates to the combination of a compound of formula (I) with a RAF inhibitor, and also to pharmaceutical compositions comprising that type of combination.

In another embodiment, the present invention relates to the combination of a compound of formula (I) with a EGFR/HER2 inhibitor, and also to pharmaceutical compositions comprising that type of combination.

In a preferred embodiment, the present invention relates to the combination of a compound of formula (I) with a taxane, and also to pharmaceutical compositions comprising that type of combination.

In another embodiment, the present invention, relates to the combination of a compound of formula (I) with a proteasome inhibitor, an immunomodulator or an alkylating agent, and also to pharmaceutical compositions comprising that type of combination.

The combination of a compound of formula (I) with an anticancer agent may be administered simultaneously or sequentially. The administration route is preferably the oral route, and the corresponding pharmaceutical compositions may allow the instantaneous or delayed release of the active ingredients. The compounds of the combination may moreover be administered in the form of two separate pharmaceutical compositions, each containing one of the active ingredients, or in the form of a single pharmaceutical composition, in which the active ingredients are in admixture.

The compounds of the invention may also be used in combination with radiotherapy in the treatment of cancer.

Finally, the compounds of the invention may be linked to monoclonal antibodies or fragments thereof or linked to scaffold proteins that can be related or not to monoclonal antibodies.

Antibody fragments must be understood as fragments of Fv, scFv, Fab, F(ab')2, F(ab'), scFv-Fc type or diabodies, which generally have the same specificity of binding as the antibody from which they are descended. According to the present invention, antibody fragments of the invention can be obtained starting from antibodies by methods such as digestion by enzymes, such as pepsin or papain, and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

Scaffold proteins that can be related or not to monoclonal antibodies are understood to mean a protein that contains or not an immunoglobulin fold and that yields a binding capacity similar to a monoclonal antibody. The man skilled in the art knows bow to select the protein scaffold. More particularly, it is known that, to be selected, such a scaffold should display several features as follow (Skerra, *J. Mol. Recogn.* 2000. 13, 167-187): phylogenetically good conservation, robust architecture with a well-known three-dimensional molecular organization (such as, for example, crystallography or NMR), small size, no or only a low degree of post-translational modifications, easy to produce, express and purify. Such a protein scaffold can be, but without limitation, a structure selected from the group consisting in fibronectin and preferentially the tenth fibronectin type III domain (FINfn10), lipocalin, anticalin (Skerra, *J Biotechnol.* 2001, 74, 257-75), the protein Z derivative from the domain B of staphylococcal protein A, thioredoxin A or any protein with a repeated domain such as an "ankyrin repeat" (Kohl et al. *PNAS* 2003, 100, 1700-1705), "armadillo repeat", "leucine-rich repeat" or "tetratricopeptide repeat". There could also be mentioned a scaffold derivative from toxins (such, as, for example, scorpion, insect, plant or mollusc toxins) or protein inhibitors of neuronal nitric oxide synthase (PIN).

The following Preparations and Examples illustrate the invention but do not limit it in any way.

General Procedures

All reagents obtained from commercial sources were used without further purification. Anhydrous solvents were obtained from commercial sources and used without further drying.

Flash chromatography was performed on ISCO Combiflash Rf 200i with pre-packed silica-gel cartridges (RediSep® $R_f$ Gold High Performance).

Thin layer chromatography was conducted with 5×10 cm plates coated with Merck Type 60 F254 silica-gel.

Microwave heating was performed in an Anton Parr MonoWave or CEM Discover® instrument.

Preparative HPLC purifications were performed on an Armen Spot Liquid Chromatography system with a Gemini-NX® 10 μM C18, 250 mm×50 mm i.d. column running at a flow rate of 118 mL min$^{-1}$ with UV diode array detection (210-400 nm) using 25 mM aqueous $NH_4HCO_3$ solution and MeCN gas eluents unless specified otherwise.

Analytical LC-MS: The compounds of the present invention were characterized by high performance liquid chromatography-mass spectroscopy (HPLC-MS) on Agilent HP1200 with Agilent 6140 quadrupole LC/MS, operating in positive or negative ion electrospray ionisation mode. Molecular weight scan range is 100 to 1350. Parallel UV detection was done at 210 nm and 254 nm. Samples were supplied as a 1 mM solution in acetonitrile, or in tetrahydrofuran/$H_2O$ (1:1) with 5 μL loop injection. LCMS analyses were performed on two instruments, one of which was operated with basic, and the other with acidic eluents. Basic LCMS: Gemini-NX, 3 μm, C18, 50 mm×3.00 mm i.d. column at 23° C., at a flow rate of 1 mL min$^{-1}$ using 5 mM ammonium bicarbonate (Solvent A) and acetonitrile (Solvent B) with a gradient starting from 100% Solvent A and finishing at 100% Solvent B over various/certain duration of time.

Acidic LCMS: ZORBAX Eclipse XDB-C18, 1.8 μm, 50 mm×4.6 mm i.d. column at 40° C., at a flow rate of 1 mL·min$^{-1}$ using 0.02% v/v aqueous formic acid (Solvent A) and 0.02%, v/v formic acid in acetonitrile (Solvent B) with a gradient starting from 100 Solvent A and finishing at 100% Solvent B over various/certain duration of time.

$^1$H-NMR measurements were performed on Bruker Avance III 500 MHz spectrometer and Bruker Avance III 400 MHz spectrometer, using DMSO-$d_6$ or $CDCl_3$ as solvent. $^1$H NMR data is in the form of delta values, given in part per million (ppm), using the residual peak of the solvent (2.50 ppm for DMSO-$d_6$, and 7.26 ppm for $CDCl_3$) as internal standard. Splitting patterns are designated as: s (singlet), d (doublet), t (triplet), q (quartet), quint (quintet), m (multiple), br s (broad singlet), dd (doublet of doublets), td (triplet of doublets), dt (doublet of triplets), ddd (doublet of doublet of doublets).

Combination gas chromatography and low resolution mass spectrometry were performed on Agilent 6850 gas chromatograph and Agilent 5975C mass spectrometer using 15 m×0.25 mm column with 0.25 μm HP-5MS coating and helium as carrier gas. Ion source: EI+, 70 eV, 230° C., quadrupole: 150° C., interface: 300° C.

HRMS were determined on a Shimadzu IT-TOP, ion source temperature 200° C., ESI+/−, ionization voltage: (+/−)4.5 kV. Mass resolution min. 10000.

Elementary analyses were performed on a Thermo Flash EA 1112 Elemental Analyzer.

EXAMPLE 1

{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl hydrogen phosphate

Step A 4-methoxybenzyl (2R)-2-{[(5S$_a$)-5-{3-chloro-2-methyl-4-[2-(4-methylpiperazin-1-yl)ethoxy]phenyl}-6-(4-fluorophenyl)thieno[2,3-]pyrimidin-4-yl}oxy]-3-(2-[[2-2-methoxyphenyl)pyrimidin-4-yl]methoxy]phenyl)propanoate 1.75 g (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid (2 mmol, 1 eq.; synthesized according to WO 2015/097123), 1.05 g triphenylphosphine (4 mmol, 2 eq.) and 0.5 mL 4-methoxy benzyl alcohol (4 mmol, 2 eq.) were dissolved in 20 mL dry toluene, then 0.92 g di-tert-butyl azodicarboxylate (4 mmol, 2 eq.) was added over 3 minutes. The resulting mixture was stirred at 50° C. until no further conversion was observed. The reaction mixture was injected directly onto a preconditioned 120 g silica column, then it was purified by flash chomatography using ethyl acetate/methanol (containing 1.2% NH$_3$) as eluent, to obtain a white crystal, $^1$H NMR (400 MHz, CDCl$_3$): 8.63 (d, 1H), 8.45 (s, 1H), 7.68 (dd, 1H), 7.59 (d, 1H), 7.45 (t, 1H), 7.28 (s, 1H), 7.21-7.13 (m, 5H), 7.10-7.04 (m, 2H), 6.99-6.80 (m, 7H), 6.24 (d, 1H), 5.68 (dd, 1H), 5.25-5.16 (m, 3H), 5.09 (d, 1H), 4.29-4.18 (m, 2H), 3.88 (s, 3H), 3.81 (s, 3H), 3.38 (dd, 2H), 2.96-2.89 (m, 2H), 2.69 (br s, 4H), 2.56 (dd, 2H), 2.46 (br s, 4H), 2.28 (s, 3H), 1.90 (s, 3H)

Step B tert-butyl [4-[2-[2-2-chloro-4-[6-(4-fluorophenyl)-4-[(1R)-2-[(4-methoxyphenyl) methoxy]-1-[[2-[[2-(2-methoxyphenyl)pyrimidin-4-yl]methoxy]phenyl]methyl]-2-oxo-ethoxy]-(5S$_a$)-thieno[2,3-d]pyrimidin-5-yl]-3-methyl-phenoxy]ethyl]-1-methyl-piperazin-1-ium-1-yl]methyl phosphate 249 mg 4-methoxybenzyl (2R)-2-{[(5S$_a$)-5-{3-chloro-2-methyl-4-[2-(4-methylpiperazin-1-yl)ethoxy]phenyl}6-(4-fluorophenyl)thieno[2,3-d]pyrimidin-4-yl]oxy}-3-(2-{[2-(2-methoxyphenyl)pyrimidin-4-yl]methoxy}phenyl) propanoate (0.25 mmol, 1 eq.), 194 mg di-tert-butyl chloromethyl phosphate (0.75 mmol, 3 eq.), 112 mg sodium iodide (0.75 mmol, 3 eq.) and 62 mg NaHCO$_3$ (0.75 mmol, 3 eq.) were stirred in 3 mL dry acetone at room temperature overnight (excluded from light). To the reaction mixture, 2 mL water was added and it was injected directly onto a RP18 column using acetonitrile/5 mM NH$_4$HCO$_3$ as eluents with gradient method. After lyophilization, a white solid is obtained. $^1$H NMR (400 MHz, CDCl$_3$): 8.64 (d, 1H), 8.46 (s, 1H), 7.68 (dd, 1H), 7.59 (d, 1H), 7.45 (t, 1H), 7.32 (d, 1H), 7.21-7.16 (m, 5H), 7.11-7.05 (m, 2H), 6.98 (t, 2H), 6.89-6.79 (m, 5H), 6.22 (d, 1H), 5.66 (dd, 1H), 5.20 (dd, 2H), 5.15 (dd, 2H), 5.08 (d, 1H), 4.26-4.16 (m, 2H), 3.88 (s, 3H), 3.81 (s, 3H), 3.70-3.65 (m, 2H), 3.38 (dd, 2H), 3.32 (br s, 1H), 3.19-3.09 (m, 1H), 3.15 (s, 3H), 3.00 (t, 2H), 2.98-2.91 (m, 2H), 2.55 (dd, 1H), 1.90 (s, 3H), 1.87 (br s, 4H), 1.46 (s, 9H)

Step C

Example 1

To 150 mg tert-butyl [4-[2-[2-2-chloro-4-[6-(4-fluorophenyl)-4-[(1R)-2-[(4-methoxyphenyl) methoxy]-1-[[2-[[2-(2-methoxyphenyl)pyrimidin-4-yl]methoxy]phenyl]methyl]-2-oxo-ethoxy]-(5S$_a$)-thieno[2,3-d]pyrimidin-5-yl]-3-methyl-phenoxy]ethyl]-1-methyl-piperazin-1-ium-1-yl]methyl phosphate (0.13 mmol, 1 eq.) dissolved in 4 mL dry dichloromethane, 0.5 mL trifluoroacetic acid (6.6 mmol 50 eq.) was added and the mixture stirred at room temperature until no further conversion was observed. The reaction mixture was evaporated to dryness, then it was purified by reverse phase chromatography using acetonitrile/5 mM NH$_4$HCO$_3$ eluents. After lyophilization, Example 1 is obtained as a white solid. HRMS calculated for C$_{48}$H$_{48}$ClFN$_6$O$_{10}$PS: 984.2485; found 471.1189 (M+2H).

EXAMPLE 2 benzyl {4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl phosphate

Step A benzyl [4-(2-[2-chloro-4-[6-(4-fluorophenyl)-4-{[(2R)-1-[(4-methoxybenzyl)oxy]-3-(2-{[2-(2-methoxyphenyl)pyrimidin-4-yl]methoxy}phenyl)-1-oxopropan-2-yl]oxy}-(5S$_a$)-thieno[2,3-d]pyrimidin-5-yl]-3-methylphenoxy}ethyl)-1-methylpiperazin-1-ium-1-yl]methyl phosphate 995 mg 4-methoxybenzyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoate (1 mmol, eq.) and 392 mg dibenzyl chloromethyl phosphate (1.2 mmol, 1.2 eq.) were stirred in 5 mL dry acetonitrile at 80° C. until no further conversion was observed. The reaction mixture was injected directly onto a preconditioned 80 g silica column, then it was purified by flash chomatography using ethyl acetate/methanol (containing 1.21% NH$_3$) as eluent. Product was obtained as an off-white crystal. $^1$H NMR (500 MHz, DMSO-d$_6$) 8.66 (d, 1H), 8.54 (s, 1H), 7.52 (d, 1H), 7.49 (dd, 1H), 7.45 (tm, 1H), 7.34-7.2 (m, 5H), 7.29 (m, 2H), 7.24 (d, 1H), 7.22 (m, 2H), 7.19 (m, 1H), 7.15 (m, 2H), 7.14 (m, 1H), 7.12 (d, 1H), 7.04 (m, 1H), 7.02 (tm, 1H), 6.88 (d, 2H), 6.74 (t, 1H), 6.21 (d, 1H), 5.55 (dd, 1H), 5.23 (d, 1H), 5.17 (d, 1H), 5.10 (d, 1H), 5.01 (d, 1H), 4.86 (d, 2H), 4.75 (d, 2H), 4.26-4.14 (m, 2H), 3.74 (s, 3H), 3.72 (s, 3H), 3.38-3.22 (m, 4H), 3.22-2.54 (m, 2H), 2.96-2.74 (br s, 4H), 2.93 (s, 3H), 2.87 (t, 2H), 1.84 (s, 3H)

Step B

Example 2

435 mg benzyl [4-(2-{2-chloro-4-[6-(4-fluorophenyl)-4-{[(2R)-1-[(4-methoxybenzyl)oxy]-3-(2-{[2-(2-methoxyphenyl)pyrimidin-4-yl]methoxy}phenyl)-1-oxopropan-2-yl]oxy}-(5S$_a$)-thieno[2,3-d]pyrimidin-5-yl]-3-methylphenoxy}ethyl)-1-methylpiperazin-1-ium-1-yl] methyl phosphate (0.36 mmol, 1 eq.) and 560 μL trifluoroacetic acid. (7.28 mmol, 20 eq.) were stirred at room temperature until no further conversion was observed. The reaction mixture was evaporated to dryness then it was purified by reversed phase chromatography using acetonitrile/5 mM NH$_4$HCO$_3$ as eluents. After lyophilization, Example 2 was obtained as a white solid. HRMS calculated for C$_{55}$H$_{55}$ClFN$_6$O$_{10}$PS: 1074.2954; found 538.1565 (M+2H).

In the following Examples 3 and 4, the procedure is as in Example 1, using the appropriate chloride derivative of formula (IV) and the appropriate thienopyrimidine compound of formula (II).

EXAMPLE 3

{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl phosphate

EXAMPLE 4

{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl hydrogen phosphate

EXAMPLE 5

{4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}methyl hydrogen phosphate

Step A 4-methoxybenzyl (2R)-2-{[(5S$_a$)-5-{3-bromo-2-methyl-4-[2-(4-methylpiperazin-1-yl)ethoxy]phenyl}-6-(4-fluorophenyl)thieno[2,3-d]pyrimidin-4-yl]oxy}-3-(2-[{2-2-methoxyphenyl)pyrimidin-4-yl]methoxy}phenyl)propanoate 1.75 g (2R)-2-{[(5S$_a$)-5-{3-bromo-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid (2 mmol, 1 eq.; synthesized according to WO 2015/097123), 1.05 g triphenylphosphine (4 mmol, 2 eq.) and 0.5 mL 4-methoxybenzyl alcohol (4 mmol, 2 eq.) were dissolved in 20 mL dry toluene, then 0.92 g di-tert-butyl azodicarboxylate (4 mmol, 2 eq.) was added over 3 minutes. The resulting mixture was stirred at 50° C. until no further conversion was observed. The reaction mixture was injected directly onto is a preconditioned 120 g silica column, then it was purified by flash chomatography using ethyl acetate/methanol (containing 1.2% NH$_3$) as eluent, to obtain a white crystal. $^1$H NMR (400 MHz, CDCl$_3$): 8.63 (d, 1H), 8.45 (s, 1H), 7.68 (dd, 1H), 7.59 (d, 1H), 7.45 (t, 1H), 7.28 (s, 1H), 7.21-7.13 (m, 5H), 7.10-7.04 (m, 2H), 6.99-6.80 (m, 7H), 6.24 (d, 1H), 5.68 (dd, 1H), 5.25-5.16 (m, 3H), 5.09 (d, 1H), 4.29-4.18 (m, 2H), 3.88 (s, 3H), 3.81 (s, 3H), 3.38 (dd, 1H), 2.96-2.89 (m, 2H), 2.69 (br s, 4H), 2.56 (dd, 2H), 2.46 (br s, 4H), 2.28 (s, 3H), 1.90 (s, 3H)

Step B tert-butyl [4-[2-[2-2-bromo-4-[6-(4-fluorophenyl)-4-[(1R)-2-[(4-methoxyphenyl) methoxy]-1-[[2-[[2-(2-methoxyphenyl)pyrimidin-4-yl]methoxy]phenyl] methyl]-2-oxo-ethoxy]-(5S$_a$)-thieno[2,3-d] pyrimidin-5-yl]-3-methyl-phenoxy]ethyl]-1-methyl-piperazin-1-ium-1-yl]methyl phosphate 265 mg compound of Step A above (0.25 mmol, 1 eq.) 194 mg di-tert-butyl chloromethyl phosphate (0.75 mmol, 3 eq.), 112 mg sodium iodide (1.75 mmol, 3 eq.) and 62 mg NaHCO$_3$ (0.75 mmol, 3 eq.) were stirred in 3 mL dry acetone at room temperature overnight (excluded from light). To the react to mixture, 2 mL water was added and it was injected directly onto a RP18 column using acetonitrile/5 mM NH$_4$HCO$_3$ as eluents with gradient method. After lyophilization, a white solid is obtained. $^1$H NMR (400 MHz, CDCl$_3$): 8.64 (d, 1H), 8.46 (s, 1H), 7.68 (dd, 1H), 7.59 (d, 1H), 7.45 (t, 1H), 7.32 (d, 1H), 7.21-7.16 (m, 5H), 7.11-7.05 (m, 2H), 6.98 (t, 2H), 6.89-6.79 (m, 5H), 6.22 (d, 1H), 5.66 (dd, 1H), 5.20 (dd, 2H), 5.15 (dd, 2H), 5.08 (d, 1H), 4.26-4.16 (m, 2H), 3.88 (s, 3H), 3.81 (s, 3H), 3.70-3.65 (m, 2H), 3.38 (dd, 2H), 3.32 (br s, 1H), 3.19-3.09 (m, 1H), 3.15 (s, 3H), 3.00 (t, 2H), 2.98-2.91 (m, 2H), 2.55 (dd, 1H), 1.90 (s, 3H), 1.87 (br s, 4H), 1.46 (s, 9H)

Step C

Example 5

150 mg compound of Step B above (0.13 mmol, 1 eq.) dissolved in 4 mL dry dichloromethane, 0.5 mL trifluoroacetic acid (6.6 mmol, 50 eq.) was added and the mixture stirred at room temperature until no further conversion was observed. The reaction was evaporated to dryness, then it was purified by reversed phase chromatography using acetonitrile/5 mM NH$_4$HCO$_3$ as eluents. After lyophilization, Example 5 was obtained. HRMS calculated for C$_{47}$H$_{44}$ClFN$_6$O$_{10}$PS: 1048.1433; found 525.0791 (M+2H).

EXAMPLE 6 benzyl {4-[2-(3-bromo-4-{(5S$_a$)-4-[(1R)-1-carboxy-2-(2-{[2-(2-methoxy phenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}methyl phosphate

Step A benzyl [4-(2-[3-bromo-2-chloro-4-[6-(4-fluorophenyl)-4-{[(2R)-1-[(4-methoxybenzyl)oxy]-3-(2-{[2-(2-methoxyphenyl)pyrimidin-4-yl]methoxy}phenyl)-1-oxopropan-2-yl]oxy}thieno[2,3-d]pyrimidin-5-yl]phenoxy]ethyl)-1-methylpiperazin-1-ium-1-yl] methyl phosphate 318 mg of compound obtained in Step A of Example 5 (0.30 mmol, 1 eq.) and 147 mg dibenzyl chloromethyl phosphate (0.45 mmol, 1.5 eq) were stirred in 1.5 mL dry acetonitrile at 70° C. until no further conversion was observed. The reaction mixture was injected directly onto a preconditioned 80 g silica column, then it was purified by flash chomatography using ethyl acetate/methanol (containing 1.2% NH$_3$) as eluent. Product of Step A was obtained as white crystals. MS: M+H=1260.6

Step B

Example 6

To the solution of 275 mg compound of Step B above (0.218 mmol, 1 eq.) in 3.5 mL dichloromethane 334 μL trifluoroacetic acid was added and the reaction mixture was stirred at room temperature until no further conversion was observed. The reaction mixture was concentrated and the crude product was purified by flash chromatography using ethyl acetate/methanol (containing 1.2% NH$_3$) as eluent. This product was then purified by reversed phase chromatography using 25 mM aqueous NH$_4$HCO$_3$ solution and MeCN as eluents. After lyophilization Example 6 was obtained as a white solid. HRMS calculated for C$_{54}$H$_{50}$BrClFN$_6$O$_{10}$PS: 1138.1903; found 570.1018 (M+2H).

EXAMPLE 7

{4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}methyl methyl phosphate In the Example 7, the procedure is as in Example 1, using the appropriate chloride derivative of formula (IV) and the appropriate thienopyrimidine compound of formula (II).

EXAMPLE 8

N-[(5S$_a$)-5-{3-chloro-4-[2-(4-{[(hydroxyphosphinato)oxy]methyl}-4-methylpiperazin-4-ium-1-yl)ethoxy]-2-methylphenyl}-6-(4-fluorophenyl)thieno[2,3-d]pyrimidin-4-yl]-2-{[2-(2-methoxyphenyl)pyrimidin-4-yl]methoxy}-D-phenylalanine Step A 6-Iodo-3H-thieno[2,3-d]pyrimidin-4-one A 2 L round bottomed flask equipped with mechanical stirrer, thermometer and reflux condenser was charged with the solution of 433 mL acetic acid, 13 mL sulfuric acid and 87 mL water. 69.3 g 3H-thieno[2,3-d]pyrimidin-4-one (0.46 mol), 51.9 g periodic acid (0.23 mol) and 104 g iodine (0.41 mol) were added to the stirred solution, which was heated to 60° C. for 1 hour. The resulting suspension was cooled to room temperature, filtered off, washed with a mixture of acetic acid and water (5:1) and then with diethyl ether. The resulting beige crystalline solid was air dried. $^1$H NMR (500 MHz, DMSO-d$_6$) δ: 12.57 (br s, 1H), 8.09 (s, 1H), 7.65 (s, 1H)

Step B

4-Chloro-6-iodo-thieno[2,3-d]pyrimidine

A 1 L round bottomed flask equipped with mechanical stirrer, thermometer, reflux condenser and a CaCl$_2$-tube was charged with 113 mL phosphorous oxychloride and 35 mL N,N-dimethylaniline (0.29 mol). 75.54 g compound of Step A above (0.27 mol) was added to the mixture in portions during 5 minutes. The reaction mixture was stirred at 105° C. for 1 hour. The resulting suspension was cooled to 10° C., filtered and washed with hexane. The crude product was added to ice water and stirred for 10 minutes, filtered off, washed with cold water, diethyl ether and air dried. Beige crystalline solid was obtained. $^1$H NMR (400 MHz, DMSO-d$_6$) δ: 8.89 (s, 1H), 7.98 (s, 1H)

Step C

5-Bromo-4-chloro-6-iodo-thieno[2,3-d]pyrimidine

A 2 L round bottomed flask equipped with mechanical stirrer, thermometer and a bubbler was charged with 600 mL acetonitrile. 84.9 g compound of Step B above (0.29 mol), 50.9 g N-bromosuccinimide (0.29 mol) and 8.5 mL tetrafluoroboric acid diethyl ether complex were added. The reaction mixture was stirred at room temperature for 16 hours. Further 22.9 g (0.12 mol) N-bromosuccinimide was added to the mixture in three portions. After cooling the suspension to 0° C. and stirring for further 1 hour the precipitate was filtered off, washed with acetonitrile and air dried. The product was obtain as beige crystalline solid. $^1$H NMR (500 MHz, DMSO-d$_6$) δ: 8.85 (s, 1H)

Step D

5-Bromo-4-chloro-6-(4-fluorophenyl)thieno[2,3-d]pyrimidine 75.08 g compound of Step C above (200 mmol), 53.63 g 2-(4-fluorophenyl)-4,5,5,5-tetramethyl-1,3,2-dioxaborolane (240 mmol), 130 g cesium carbonate (400 mmol) 2.245 g Pd(OAc)$_2$ (10 mmol) and 8.50 g 2-di-tert-butylphosphino-2',4',6'-triisopropylbiphenyl 20 mmol) were placed in a 2 L flask. 600 mL tetrahydrofuran and 200 mL water were added, and then stirred over night at 70° C. under argon. Tetrahydrofuran was evaporated, and then the product was collected by filtration. The crude product was sonicated in 250 mL acetonitrile and filtered again. Then 5-bromo-4-chloro-6-(4-fluorophenyl)thieno[2,3-d]pyrimidine as crystalized from ethanol/tetrahydrofuran (2:1). $^1$H NM R (400 MHz, DMSO-d$_6$) δ: 9.02 (s, 1H), 7.80-7.77 (m, 2H), 7.47-7.43 (m, 2H)

Step E (2R)-2-[[5-Bromo-6-(4-fluorophenyl)thieno[2,3-d]pyrimidin-4-]amino]-3-(2-hydroxyphenyl)propanoic acid 1 eq. of compound of Step D above, 2 eq. of (2R)-2-amino-3-(2-hydroxyphenyl)propanoic acid and 3 eq. K$_2$CO$_3$ were mixed in dimethyl sulfoxide (10 mL/mmol) and stirred at 50° C. until no further conversion was observed. The mixture was then diluted with water, acidified with 1M HCl solution (to pH=1, or to pH=6 in the presence of a basic amino group) and extracted with ethyl acetate, or the precipitate formed after acidification was isolated by filtration. The crude product was purified via preparative reversed phase chromatography using 25 mM aqueous NH$_4$HCO$_3$ and acetonitrile eluents to give (2R)-2-[[5-bromo-6-(4-fluorophenyl)thieno[2,3-d]pyrimidin-4-yl]amino]-3-(2-hydroxyphenyl) propanoic acid.

$^1$H NMR (400 MHz, DMSO-d$_6$) δ: 12.90 (br s, 1H), 9.65 (br s, 1H), 8.41 (s, 1H), 7.70 (m, 2H), 7.45-7.34 (m 3H), 7.18 (dd, 1H), 7.04 (td, 1H), 6.80 (d, 1H), 6.72 (t, 1H), 4.96 (m, 1H), 3.31 (dd, 1H), 3.08 (dd, 1H)
MS (M+H): 488.0

Step F (4-Bromo-2-chloro-phenoxy)-trimethyl-silane 20.8 g 4-bromo-2-chloro-phenol (100 mmol) was dissolved in 150 mL dry tetrahydrofuran then 24.2 g hexamethyldisilazane (150 mmol) was added. The reaction mixture was stirred at 85° C. under argon atmosphere for 1.5 hours then concentrated under reduced pressure. The resulted crude product was used without further purification. $^1$H NMR (200 MHz, CDCl$_3$) δ: 7.49 (d, 1H), 7.23 (dd, 1H), 6.75 (d, 1H), 0.26 (s, 9H)

Step G

4-Bromo-2-chloro-3-methyl-phenol 48 mL n-butyl lithium solution (120 mmol, 2.5 M in hexanes) was added dropwise to a solution of 12.1 g dry diisopropylamine (120 mmol) in 250 mL dry tetrahydrofuran at –78° C. under argon atmosphere. The mixture was stirred for 30 minutes at the same temperature then 28.0 g compound of Step F above (100 mmol) was added dropwise. After 2.5 hours, 21.3 g methyl iodide (150 mmol) was added dropwise then the cooling bath was removed and the mixture was stirred overnight. The reaction was quenched with 100 mL NH$_4$OH solution and 200 mL NH$_4$Cl solution then extracted with ethyl acetate. The organic phase was dried over Na$_2$SO$_4$, filtered and the filtrate was concentrated under reduced pressure. The resulting dark mass was refluxed with pure hexane several times (150-150 mL aliquots) and decanted leaving a black tar behind. The combined organic phases were concentrated under reduced pressure affording 19.0 g crude product, which was used without further purification, $^1$H NMR (200 MHz, CDCl$_3$) δ: 7.32 (d, 1H), 6.76 (d, 1H), 5.62 (s, 1H), 2.49 (s, 3H)

Step H (4-Bromo-2-chloro-3-methyl-phenoxy)-trimethyl-silane 20.8 g hexamethyldisilazane (129 mmol) was added to the solution of 19.0 g compound of Step H above (86.0 mmol) in 150 mL dry tetrahydrofuran. The mixture was stirred at 85° C. under argon balloon for 1.5 hours and then concentrated under reduced pressure. The obtained product was used without further purification, $^1$H NMR (200 MHz, CDCl$_1$) δ: 7.30 (d, 1H), 6.63 (d, 1H), 2.50 (s, 3H), 0.28 (s, 9H)

Step I

2-Chloro-3-methyl-4-(4,4,5,5-tetramethyl-1,3,2-dioxaborolan-2-yl)phenol

A solution of 25.2 g compound of Step H above (86.0 mmol) in 250 mL dry tetrahydrofuran was cooled to –78° C. under argon and then 38 mL n-butyl lithium solution (94.6 mmol, 2.5M in hexanes) was added dropwise. After 5 minutes, 19.2 g 2-isopropoxy-4,4,5,5-tetramethyl-1,3,2-dioxaborolane (1.03 mmol) was added dropwise. The cooling bath was removed and the mixture was slowly allowed to warm up to room temperature. Then the mixture was added to 200 mL NH$_4$Cl solution and extracted with ethyl acetate. The combined organic layers were concentrated under reduced pressure and passed through a pad of silica gel using hexane and ethyl acetate as eluents. The crude product was recrystallized from a mixture of ethyl acetate and hexane to obtain 2-chloro-3-methyl-4-(4,4,5,5-tetramethyl-1,3,2-dioxaborolan-2-yl)phenol. $^1$H NMR (500 MHz, DMSO-d$_6$) δ: 10.40 (s, 1H), 7.42 (d, 1H), 6.80 (d, 2.49 (s, 3H), 1.27 (s, 12H)

Step J

1-[2-[2-Chloro-3-methyl-4-(4,4,5,5-tetramethyl-1,3,2-dioxaborolan-2-yl)phenoxy]ethyl]-4-methyl-piperazine 10.0 g compound of Step I above (37.2 mmol), 8.7 g 2-(4-methylpiperazin-1-yl)ethanol (60.3 mmol) and 15.8 g triphenylphosphine (60.3 mmol) were dissolved in 100 mL dry toluene and then 27 mL diethyl azodicarboxylate (60.3 mmol, 40% solution in toluene) was added dropwise. The mixture was stirred at 50° C. under argon until no further conversion was observed. The volatiles were evaporated under reduced pressure and 100 mL diethyl ether was added. The precipitated white crystals were filtered off and washed with diethyl ether. The filtrate was concentrated under reduced pressure and purified via flash chromatography using chloroform and methanol as eluents. The resulting light brown oil was crystallized from hexane to give 1-[2-[2-chloro-3-methyl-4-(4,4,5,5-tetramethyl-1,3,2-dioxaborolan-2-yl)phenoxy]ethyl]-4-methyl-piperazine as an off-white solid. $^1$H NMR (500 MHz, DMSO-d$_6$) δ: 7.56 (d, 1H), 6.99 (d, 1H), 4.15 (t, 2H), 2.72 (t, 2H), 2.51 (s, 3H), 2.50 (br s, 4H), 2.29 (br s, 4H), 2.13 (s, 3H), 1.29 (s, 12H)

Step K (2R)-2-[[(5S$_a$)-5-[3-Chloro-2-methyl-4-[2-(4-methylpiperazin-1-yl)ethoxy]phenyl]-6-(4-fluorophenyl)thieno[2,3-d]pyrimidin-4-yl]amino]-3-(2-hydroxyphenyl)propanoic acid 1 eq. of compound of Step E above and 3 eq. of compound of Step J above were dissolved in dioxane:water 2:1 mixture (10 mL/mmol), then 2 eq. Cs$_2$CO$_3$, 5 mol % Pd(OAc)$_2$ and 0.2 eq. tri-tert-butylphosphonium tetrafluoroborate were added and the mixture was stirred at 120° C. in microwave reactor under nitrogen until no further conversion was observed. The mixture was neutralized with 1M HCl solution and extracted with dichloromethane. The combined organic phases ere dried over Na$_2$SO$_4$, filtered and the filtrate was concentrated in vacuo. The crude product as purified via preparative reversed phase chromatography using 0.1 aqueous trifluoroacetic acid solution and acetonitrile as eluents to give (2R)-2-[[5-[3-chloro-2-methyl-4-[2-(4-methylpiperazine-1-yl)ethoxy]phenyl]-6-(4-fluorophenyl)thieno[2,3-d]pyrimidin-4-yl]amino]-3-(2-hydroxyphenyl) propanoic acid as a mixture of diastereomers. The mixture was separated via flash chromatography using HILIC eluents. The earlier eluting diastereoisomer was collected as (2R)-2-[[(5R$_a$)-5-[3-chloro-2-methyl-4-[2-(4-methylpiperazin-1-yl)ethoxy]phenyl]-6-(4-fluorophenyl)thieno[2,3-d]pyrimidin-4-yl]amino]-3-(2-hydroxyphenyl)propanoic acid. MS (M+H): 676.2

The later eluting diastereoisomer was collected as (2R)-2-[[(5S$_a$)-5-[3-chloro-2-methyl-4-[2-(4-methylpiperazin-1-yl)ethoxy]phenyl]-6-(4-fluorophenyl)thieno[2,3-d]pyrimidin-4-yl]amino]-3-(2-hydroxyphenyl)propanoic acid. MS (M+H): 676.2

Step L

Ethyl (2R)-2-[[(5S$_a$)-5-[3-chloro-2-methyl-4-[2-(4-methylpiperazin-1-yl)ethoxy]phenyl]-6-(4-fluorophenyl)thieno[2,3-d]pyrimidin-4-yl]amino]-3-(2-hydroxyphenyl) propanoate 4.51 g of (2R)-2-[[(5S$_a$)-5-[3-chloro-2-methyl-4-[2-(4-methylpiperazin-1-yl)ethoxy]phenyl]-6-(4-fluorophenyl)thieno[2,3-d]pyrimidin-4-yl]amino]-3-(2-hydroxyphenyl) propanoic acid (6.67 mmol) was, dissolved in 85 mL. 1.25M HCl in ethanol and stirred at 40° C. overnight. The mixture was then cautiously diluted with NaHCO$_3$ solution and extracted with dichloromethane. The combined organic phases were dried over Na$_2$SO$_4$, filtered and concentrated in vacuo. The crude product was purified via flash chromatography using dichloromethane and methanol as eluents to obtain ethyl (2R)-2-[[(5S$_a$)-5-[3-chloro-2-methyl-4-[2-(4-methylpiperazin-1-yl)ethoxy]phenyl]-6-(4-fluorophenyl)thieno[2,3-d]pyrimidin-4-yl]amino]-3-(2-hydroxyphenyl) propanoate. $^1$H NMR (500 MHz, DMSO-d$_6$) δ: 9.49 (s, 1H), 8.40 (s, 1H), 7.34 (d, 1H), 7.27-7.21 (m, 3H), 7.20-7.14 (m, 2H), 7.00 (td, 1H), 6.71 (dd, 1H), 6.60 (td, 1H), 6.39 (dd, 1H), 5.03 (d, 1H), 4.92 (m, 1H), 4.26 (t, 2H), 4.03 (m, 2H), 3.03 (dd, 1H), 2.78 (t, 2H), 2.54 (br, 4H), 2.36 (dd, 1H), 2.30 (br, 4H), 2.12 (s, 3H), 1.83 (s, 3H), 1.10 (t, 3H) HRMS calculated for C$_{37}$H$_{39}$ClFN$_5$O$_4$S: 703.2395; found 704.2450 (M+H).

Step M (E)-4-(Dimethylamino)-1,1-dimethoxy-but-3-en-2-one 502.1 g 1,1-dimethoxypropan-2-one (4.25 mol) and 506.4 g 1,1-dimethoxy-N,N-dimethyl-methanamine (4.25 mol) were mixed in a 2 L flask and stirred at 105° C. for 3 hours. The formed methanol was removed continuously via distillation. When menthol for stopped (at 65° C. head temperature) the reaction mixture was vacuum distilled (decreasing the pressure slowly to 30 mbar to remove side products and unreacted starting materials. The crude product as distilled at 0.1 mbar. Fractions were collected between 107-118° C. head temperature (bath temperature 160-165° C.) to give a yellow oil. $^1$H NMR (500 MHz, DMSO-d$_6$) δ: 7.59 (d, 1H), 5.17 (d, 1H), 4.42 (s, 1H), 3.25 (s, 6H), 3.09 (s, 3H), 2.78 (s, 3H)

Step N 4-(Dimethoxymethyl)-2-(2-methoxyphenyl)pyrimidine

To the mixture of 1.2 eq. of 2-methoxybenzamidine acetic acid sale and 1 eq. of compound of Step M above in dry methanol (0.5 mL/mmol), 1.2 eq. sodium methoxide was added portionwise and the mixture was stirred at 75° C. until no further conversion was observed. The reaction mixture was cooled and concentrated under reduced pressure. Water was added to the residue, and it as extracted with dichloromethane. The combined organic layers dried over MgSO$_4$, filtered and the filtrate was concentrated under reduced press. The crude product was purified via flash chromatography using heptane and ethyl acetate as eluents to give 4-(dimethoxymethyl)-2-(2-methoxyphenyl)pyrimidine, $^1$H NMR (400 MHz, DMSO-d$_6$) δ: 8.93 (d, 1H), 7.55-7.44 (m, 3H), 7.16 (d, 1H), 7.06 (m, 1H), 5.31 (s, 1H), 3.76 (s, 3H), 3.37 (s, 6H)

Step O

[2-(2-Methoxyphenyl)pyrimidin-4-yl]methanol 261 mg compound of Step N above (1.0 mmol) gas dissolved in 2 mL 4M HCl solution (in dioxane), then 2 mL water as added and this mixture was stirred at 50° C. for 16 hours. The reaction mixture was cooled to 0° C., then 320 mg NaOH (8.0 mmol) was added portionwise. The pH was adjusted to 8 using 10% K$_2$CO$_3$ solution, then 76 mg sodium borohydride (2.0 mmol) was added and the mixture was stirred for 30 minutes 0° C. The reaction mixture was diluted with 5 mL water and extracted with ethyl acetate. The combined organic phases were dried over Na$_2$SO$_4$, filtered and the filtrate was concentrated under reduced pressure. The crude product was purified via flash chromatography using heptane and ethyl acetate as eluents to give [2-(2-methoxyphenyl)pyrimidin-4-yl]methanol. $^1$H NMR (400 MHz, DMSO-d$_6$) δ: 8.84 (d, 1H), 7.50-7.42 (m, 3H), 7.14 (d, 1H), 7.03 (m, 1H), 5.66 (t, 1H), 4.58 (d, 2H), 3.75 (3H)

Step P

N-[(5S$_a$)-5-{3-Chloro-2-methyl-4-[2-(4-methylpiperazin-1-yl)ethoxy]phenyl}-6-(4-fluorophenyl)thieno[2,3-d]pyrimidin-4-yl]-2-{[2-(2-methoxyphenyl)pyrimidin-4-yl]methoxy}-D-phenylalanine 1 eq. of compound of Step L above, 2 eq. of compound of Step O above, and 3 eq. triphenylphosphine were dissolved in dry toluene (7 mL/mmol) under nitrogen atmosphere, then 3 eq. di-tert-butyl azodicarboxylate was added at room temperature. Then the mixture was stirred at 50° C. until no further conversion was observed. The volatiles were removed in vacuo and the residue was purified via flash chromatography using heptane and ethyl acetate as eluents.

1 eq. of the formed ester derivative was dissolved tetrahydrofuran (15 mL/mmol) then 10 eq. lithium hydroxide monohydrate and water (15 mL/mmol) were added. The mixture was stirred at room temperature until no further conversion was observed. The pH was adjusted to 6 with 1M HCl solution, then the mixture was diluted with brine, extracted with dichloromethane. The organic layer as dried over Na$_2$SO$_4$, filtered and the filtrate was concentrated under reduced pressure. The crude product was purified via preparative reversed phase chromatography using 25 mM aqueous NH$_4$HCO$_3$ solution and acetonitrile as eluents yield N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-{[2-(2-methoxyphenyl) pyrimidin-4-yl]methoxy}-D-phenylalanine. HRMS calculated for C$_{47}$H$_{45}$ClFN$_7$O$_5$S: 873.2875, found: 437.6498 (M+2H).

Step Q 4-methoxybenzyl N-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-2-{[2-(2-methoxyphenyl)pyrimidin-4-yl]methoxy}-D-phenylalaninate 1677 mg compound of Step P above (1.92 mmol, 1 eq.) 1.51 g triphenylphosphine (5.76 mmol, 3 eq.) and 796 mg 4-methoxybenzyl alcohol (5.76 mmol, 3 eq.) were dissolved in 20 mL dry toluene, then 1.33 g di(tert)butyl azodicarboxylate (5.76 mmol, 3 eq.) was added in one portion. The resulting mixture was stirred at 50° C. until no further conversion was observed. The reaction mixture was concentrated and the crude product was purified by flash chomatography using ethyl acetate/methanol (containing 1.2% NH$_3$) as eluent. Product of Step Q was obtained as off-white crystals. HRMS calculated for C$_{55}$H$_{53}$ClFN$_2$O$_6$S: 993.3450; found 497.6814 (M+2H).

Step R 4-methoxybenzyl N-[(5S$_a$)-5-{4-[2-(4{[(benzyloxy)phosphinato]oxy}-4-methylpiperazin-4-ium-1-yl)ethoxy]-3-chloro-2-methylphenyl}-6-(4-fluorophenyl)thieno[2,3-d]pyrimidin-4-yl]-2-{[2-(2-methoxyphenyl)pyrimidin-4-yl]methoxy}-D-phenylalaninate 300 mg compound of Step Q above (0.301 mmol, 1 eq.) and 1.48 mg dibenzyl chloromethyl phosphate (0.451 mmol, 1.5 eq.) were stirred in n 1.5 mL dry acetonitrile at 40° C. until no further conversion was observed. The reaction mixture was injected directly onto a preconditioned 24 g silica column, then it was purified by flash chomatography using ethyl acetate/methanol (containing 1.2% NH$_3$) as eluent. Compound of Step R was obtained as off-white crystals. HRMS calculated for C$_{63}$H$_{62}$ClFN$_7$O$_{10}$PS: 1193.3689; found 597.6928 (M+2H).

Step S

Example 8

To the solution of 100 mg compound of Step R above (0.0837 mmol) in 840 μL dichloromethane, 152 μL 33% HBr in acetic acid was added and it was stirred at 0° C. until no further conversion was observed. The reaction mixture was concentrated, purified by flash chomatography using ethyl acetate/methanol (containing 1.2% NH$_3$) as eluent.

Then the resulted product was purified by reversed phase chromatography using acetonitrile/5 mM NH$_4$HCO$_3$ as eluents. After lyophilization, Example 8 was obtained as a white solid. HRMS calculated for C$_{48}$H$_{48}$BrClFN$_7$O$_9$PS: 983.2645; found 492.6377 (M+2H).

EXAMPLE 9

{4-[2-(4-{4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2,6-dichloro-3,5-dimethylphenoxy)ethyl]-1-methylpiperazin-1-ium-1-yl}methyl hydrogen phosphate Step A 4-Bromo-2,6-dichloro-3,5-dimethyl-phenol 30.16 g 4-bromo-3,5-dimethyl-phenol as dissolved in a mixture of 75 mL 1,2-dichloroethane and 75 mL acetonitrile, then 40.06 g N-chlorosuccinimide (300 mmol, 20 eq.) was added portionwise and the mixture was stirred at room temperature until no further conversion was observed. Reaction mixture was concentrated under reduced pressure and the residue was dissolved in dichloromethane, washed with water and brine. The organic layer was dried over Na$_2$SO$_4$ and concentrated under reduced pressure and used in the next step without further purification. $^1$H NMR (400 MHz, DMSO-d$_6$): 10.10 (s, 1H), 2.46 (s, 6H)

Step B

1-Bromo-3,5-dichloro-4-methoxy-2,6-dimethyl-benzene

To a solution of 26.0 g compound of Step A above (96.3 mmol, 1 eq.) and 26.60 g K$_2$CO$_3$ (192.6 mmol, 2.0 eq.) in 300 mL acetonitrile, 6.6 mL methyl iodide (105.9 mmol, 1.1 eq.) was added and the mixture was stirred at room temperature until no further conversion was observed. The solids were filtered off and the filtrate was concentrated under reduced pressure. The crude product was dissolved in dichloromethane, washed with water and brine. The organic layer was dried over Na$_2$SO$_4$ and concentrated under reduced pressure and used in the next step without further purification. $^1$H NMR (400 MHz, DMSO-d$_6$): 3.78 (s, 3H), 2.49 (s, 6H)

Step C 2-(3,5-Dichloro-4-methoxy-2,6-dimethyl-phenyl)-4,4,5,5-tetramethyl-1,3,2-dioxaborolane 10.0 g compound of Step B above (35.2 mmol, 1.0 eq.) was dissolved in 360 mL dry tetrahydrofuran under nitrogen and was cooled to −78° C. with dry ice-acetone. 23.2 mL n-butyl lithium (1.6M in hexanes) (37.0 mmol, 1.05 eq.) was added and the mixture was stirred for 15 minutes, then 8.6 mL 2-isopropoxy-4,4,5,5-tetramethyl-1,3,2-dioxaborolane (42.24 mmol, 1.2 eq.) was added and the mixture was allowed to warm up to room temperature. It was quenched with brine, extracted with dichloromethane, dried over Na$_2$SO$_4$, filtered and concentrated wader reduced pressure. The crude product was purified via flash chromatography using heptane and ethyl acetate as eluents to obtain 2-(3,5-dichloro-4-methoxy-2,6-dimethyl-phenyl-4,4,5,5-tetramethyl-1,3,2-dioxaborolane. $^1$H NMR (400 MHz, DMSO-d$_6$): 3.81 (s, 3H), 2.33 (s, 6H), 1.34 (s, 12H)

Step D

Ethyl 4-(3,5-dichloro-4-methoxy-2,6-dimethyl-phenyl)thiophene-3-carboxylate 392 g ethyl 4-bromothiophene-3-carboxylate (16.68 mmol, 1.0 eq.) and 9.9 g compound of Step C above (30.0 mmol, 1.8 eq.) were dissolved in 140 mL dioxane, then 10.87 Cs$_2$CO$_3$ (33.36 mmol, 2.0 eq.) dissolved in 40 mL water was added. Then 590 mg bis(di-tert-butyl(4-dimethylaminophenyl)phosphine) dichloropalladium(II) (0.83 mmol, 0.05 eq.) was added, the mixture was stirred under nitrogen at reflux temperature until no further conversion was observed. Then it was diluted with dichloromethane and brine. After phase separation the aqueous phase was extracted with dichloromethane. The organic layers were combined and dried over Na$_2$SO$_4$, filtered and concentrated under reduced pressure. The crude product was purified via flash chromatography using heptane and ethyl acetate as eluents to obtain ethyl 4-(3,5-dichloro-4-methoxy-2,6-dimethyl-phenyl)thiophene-3-carboxylate.

$^1$H NMR (400 MHz, DMSO-d$_6$): 8.53 (d, 1H), 7.47 (d, 1H), 4.02 (q, 2H), 3.83 (s, 3H), 1.95 (s, 6H), 1.00 (t, 3H) HRMS (M+NH$_4$)$^{30}$=376.0538

Step E

Ethyl 4-(3,5-dichloro-4-methoxy-2,6-dimethyl-phenyl)-2,5-diiodo-thiophene-3-carboxylate 2.65 g compound of Step D above (7.38 mmol, 1.0 eq.) was dissolved in 75 mL acetonitrile, then 2.2 mL fluoroboric acid diethyl ether complex (16.23 mmol, 2.2 eq.) and 3.65 g N-iodosuccinimide (16.23 mmol, 2.2 eq.) was added and the mixture was stirred at room temperature until no further conversion was observed. Reaction mixture was concentrated under reduced pressure, and the crude product was purified via flash chromatography using heptane and ethyl acetate as eluents to obtain ethyl 4-(3,5-dichloro-4-methoxy-2,6-dimethyl-phenyl)-2,5-diiodo-thiophene-3-carboxylate.
$^1$H NMR (400 MHz, DMSO-$d_6$): 3.98 (q, 2H), 3.84 (s, 3H), 1.92 (s, 6H), 0.84 (t, 3H)

Step F

Ethyl 4-(3,5-dichloro-4-methoxy-2,6-dimethyl-phenyl)-5-iodo-thiophene-3-carboxylate 5.29 g compound of Step E above (8.66 mmol, 1.0 eq.) was dissolved in 67 mL dry tetrahydrofuran, then cooled to −78° C. under argon atmosphere. 6.7 mL isopropyl magnesium chloride lithium chloride complex (1.3M in tetrahydrofuran) (8.66 mmol, 1.0 eq.) was added and the mixture was stirred at −78° C. for 30 minutes. Then saturated aqueous NH$_4$Cl was added and the mixture was extracted with ethyl acetate. The organic layer was dried over Na$_2$SO$_4$ and concentrated under reduced pressure. The crude product was purified via flash chromography using heptane and ethyl acetate as eluents to obtain ethyl 4-(3,5-dichloro-4-methoxy-2,6-dimethyl-phenyl)-5-iodo-thiophene-3-carboxylate. $^1$H NMR (400 MHz, DMSO-$d_6$): 8.71 (s, 1H), 4.01 (q, 2H), 3.86 (s, 3H), 1.89 (s, 6H), 0.99 (t, 3H)

Step G

Ethyl 4-(3,5-dichloro-4-methoxy-2,6-dimethyl-phenyl)-5-(4-fluorophenyl)thiophene-3-carboxylate 4.20 g compound of Step F above (8.66 mmol, 1.0 eq.) and 1.82 g 4-fluorophenylboronic acid (13.00 mmol, 1.5 eq.) were dissolved in 80 mL dioxane, then 5.64 g Cs$_2$CO$_3$ (17.32 mmol, 2.0 eq.) dissolved in 20 mL water was added. Then 500 mg tetrakis(triphenylphosphine)palladium(0) (0.43 mmol, 1.15 eq.) was added, and the mixture was stirred under nitrogen at 80° C. until no further conversion was observed. Then it was diluted with dichloromethane and brine. After phase separation the aqueous phase was extracted with dichloromethane. The organic layers were combined and dried over Na$_2$SO$_4$, filtered and concentrated under reduced pressure. The crude product was purified via flash chromatography using heptane and ethyl acetate as eluents to obtain ethyl 4-(3,5-dichloro-4-methoxy-2,6-dimethyl-phenyl)-5-(4-fluorophenyl)thiophene-3-carboxylate.
$^1$H NMR (400 MHz, DMSO-$d_6$): 8.58 (s, 1H), 7.22-730 (m, 4H), 4.03 (q, 2H), 3.82 (s, 3H), 1.92 (s, 6H), 1.00 (t, 3H)
HRMS (M+H)$^+$=453.0498

Step H

Ethyl 4-(3,5-dichloro-4-methoxy-2,6-dimethyl-phenyl)-5-(4-fluorophenyl)-2-nitro-thiophene-3-carboxylate 1.97 g compound of Step G above (4.34 mmol, 1.0 eq.) was dissolved in 40 mL dry acetonitrile, then 576 mg nitronium tetrafluoroborate (4.34 mmol, 1.0 eq.) was added and the mixture was stirred at room temperature until no further conversion was observed. Then it was diluted with dichloromethane and brine. After phase separation the aqueous phase was extracted with dichloromethane. The organic layers were combined and dried over Na$_2$SO$_4$, filtered and concentrated under reduced pressure. The crude product was purified via flash chromatography using heptane and ethyl acetate as eluents to obtain ethyl 4-(3,5-dichloro-4-methoxy-2,6-dimethyl-phenyl)-5-(4-fluorophenyl)-2-nitro-thiophene-3-carboxylate. $^1$H NMR (400 MHz, DMSO-$d_6$): 7.37-7.33 (m, 2H), 7.32-7.26 (m, 2H), 4.14 (q, 2H), 3.82 (s, 3H), 2.06 (s, 6H), 0.88 (t, 3H)

Step I

Ethyl 2-amino-4-(3,5-dichloro-4-methoxy-2,6-dimethyl-phenyl)-5-(4-fluorophenyl)-thiophene-3-carboxylate 1.85 g compound of Step H above (3.71 mmol, 1.0 eq.) was dissolved in a mixture of 90 mL acetic acid and 18 mL water, then 2.43 g zinc dust (37.1 mmol, 10 eq.) was added portionwise and the mixture was stirred at room temperature until no further conversion was observed. Reaction mixture was concentrated under reduced pressure, and the crude product was purified via flash chromatography using heptane and ethyl acetate as eluents to obtain ethyl 2-amino-4-(3,5-dichloro-4-methoxy-2,6-dimethyl-phenyl)-5-(4-fluorophenyl)thiophene-3-carboxylate.
$^1$H NMR (400 MHz, DMSO-$d_6$): 7.73 (s, 2H), 7.12-7.06 (m, 2H), 7.02-6.97 (m, 2H), 3.86-3.80 (m, 2H), 3.80 (s, 3H), 2.01 (s, 6H), 0.72 (t, 3H)
HRMS (M+H)$^+$=456.0598

Step J 5-(3,5-Dichloro-4-methoxy-2,6-dimethyl-phenyl)-6-(4-fluorophenyl)-3H-thieno[2,3-d]pyrimidin-4-one 1.10 g compound of Step I above (2.35 mmol, 1.0 eq.) was dissolved in 20 mL formamide and it was stirred at 150° C. until further conversion was observed. Then it was poured onto water and the precipitated product was collected by filtration to give 5-(3,5-dichloro-4-methoxy-2,6-dimethyl-phenyl)-6-(4-fluorophenyl)-3H-thieno[2,3-d]pyrimidin-4-one.
$^1$H NMR (400 MHz DMSO-$d_6$): 12.53 (br s, 1H), 8.18 (s, 1H), 7.23-7.16 (m, 4H), 3.84 (s, 3H), 1.96 (s, 6H)
HRMS (M+H)$^{30}$=449.0289

Step K

4-Chloro-5-(3,5-dichloro-4-methoxy-2,6-dimethyl-phenyl)-6-(4-fluorophenyl)-thieno-[2,3-d]pyrimidine 700 mg compound of Step J above (1.56 mmol, 1.0 eq.) was dissolved in 6 mL phosphorous oxychloride and it was stirred at 90° C. until no further conversion was observed. Reaction mixture was concentrated under reduced pressure, then to the crude product icy water was added and it was sonicated for 10 minutes. The precipitated product was collected by filtration to give 4-chloro-5-(3,5-dichloro-4-methoxy-2,6-dimethyl-phenyl)-6-(4-fluorophenyl)thieno[2,3-d]pyrimidine.

¹H NMR (400 MHz DMSO-d₆): 9.02 (s, 1H), 7.38-7.26 (m, 4H), 3.86 (s, 3H), 1.99 (s, 6H), HRMS (M+H)⁺=466.9954

Step L 2,6-Dichloro-4-[4-chloro-6-(4-fluorophenyl)thieno[2,3-d]pyrimidin-5-yl]-3,5-dimethyl-phenol and 4-[4-bromo-6-(4-fluorophenyl)thieno[2,3-d]pyrimidin-5-yl]-2,6-dichloro-3,5-dimethyl-phenol To a stirred solution of 700 mg compound of Step K above (1.50 mmol, 1.0 eq.) in 15 mL dichloromethane, 3.0 mL boron tribromide (1M in dichloromethane) (3.0 mmol, 2.0 eq.) was added at 0° C., and the mixture was allowed to warm up to room temperature and it was stirred until no further conversion was observed. The mixture was quenched with saturated aqueous NH₄Cl and extracted with dichloromethane. The combined organic phases were dried over Na₂SO₄ and concentrated under reduced pressure. The residue was purified via flash chromatography using heptane and ethyl acetate as eluents to obtain 2,6-dichloro-4-[4-chloro-6-(4-fluorophenyl)thieno[2,3-d]pyrimidin-5-yl]-3,5-dimethyl-phenol and 4-[4-bromo-6-(4-fluorophenyl)thieno[2,3-d]pyrimidin-5-yl]-2,6-dichloro-3,5-dimethyl-phenol as a 37:63 mixture of products.

¹H NMR (400 MHz, DMSO-d₆): 10.14 (br s, 1H), 9.01 (s, 1H), 7.40-7.23 (m, 4H), 1.95 (s, 6H) and 10.14 (br s, 1H), 8.93 (s, 1H), 7.40-7.23 (m, 4H), 1.93 (s, 6H)

HRMS (M+H)⁺=452.9800 and 496.9287

Step M

4-Chloro-5-[3,5-dichloro-2,6-dimethyl-4-[2-(4-methylpiperazin-1-yl)ethoxy]phenyl]-6-(4-fluorophenyl)thieno[2,3-d]pyrimidine and 4-bromo-5-[3,5-dichloro-2,6-dimethyl-4-[2-(4-methylpiperazin-1-yl)ethoxy]phenyl]-6-(4-fluorophenyl)thieno[2,3-d]pyrimidine 300 mg mixture of 2,6-dichloro-4-[4-chloro-6-(4-fluorophenyl)thieno[2,3-d]pyrimidin-5-yl]-3,5-dimethyl-phenol and 4-[4-bromo-6-(4-fluorophenyl)thieno[2,3-d]pyrimidin-5-yl]-2,6-dichloro-3,5-dimethyl-phenol (0.62 mmol), 286 mg 2-(4-methylpiperazin-1-yl)ethanol (1.98 mmol, 3.0 eq.) and 520 mg triphenyl phosphine (1.98 mmol, 3.0) were dissolved in 10 mL dry toluene, then 460 mg di-tert-butyl azodicarboxylate (1.9 mmol, 3.0 eq.) was added. The mixture was stirred at 50° C. under nitrogen until no further conversion was observed. The volatiles were evaporated under reduced pressure and the crude intermediate was purified via flash chromatography using ethyl acetate and methanol as eluents to obtain 4-chloro-5-[3,5-dichloro-2,6-dimethyl-4-[2-(4-methylpiperazin-1-yl)ethoxy]phenyl]-6-(4-fluorophenyl)thieno[2,3-d]pyrimidine and 4-bromo-5-[3,5-dichloro-2,6-dimethyl-4-[2-(4-methylpiperazin-1-yl)ethoxy]phenyl]-6-(4-fluorophenyl)thieno[2,3-d]pyrimidine as a 35:65 mixture of products.

¹H NMR (400 MHz, DMSO-d₆): 9.02 (s, 1H), 7.40-7.22 (m, 4H), 4.11 (t, 2H), 2.78 (t, 2H), 2.63-2.20 (m 8H), 2.17 (br s, 3H), 1.98 (s, 6H) and 8.94 (s, 1H), 7.40-7.22 (m, 4H), 4.11 (t, 2H), 2.78 (t, 2H), 2.63-2.20 (m, 8H), 2.15 (br s, 3H), 1.98 (s, 6H)

HRMS (M+H)³⁰=579.0968 and 623.0455

Step N

Ethyl (2R)-2-[5-[3,5-dichloro-2,6-dimethyl-4-[2-(4-methylpiperazin-1-yl)ethoxy]phenyl]-6-(4-fluorophenyl)thieno[2,3-d]pyrimidin-4-yl]oxy-3-[2-[[2-(2-methoxyphenyl)pyrimidin-4-yl]methoxy]phenyl]propanoate 200 of 4-chloro-5-[3,5-dichloro-2,6-dimethyl-4-[2-(4-methylpiperazin-1-yl) ethoxy]phenyl]-6-(4-fluorophenyl)thieno[2,3-d]pyrimidine and 4-bromo-5-[3,5-dichloro-2,6-dimethyl-4-[2-(4-methylpiperazin-1-yl)ethoxy]phenyl]-6-(4-fluorophenyl)thieno[2,3-d]pyrimidine (0.33 mmol, 1.0 eq.), 211 mg ethyl (2R)-2-hydroxy-3-[2-[[2-(2-methoxyphenyl)pyrimidin-4-yl]methoxy]phenyl]propanoate (0.52 mmol, 1.58 eq.) and 202 mg Cs₂CO₃ (0.62 mmol, 1.88 eq.) was dissolved in 5 mL tert-butanol and the mixture was stirred at 70° C. until no further conversion a was observed. It was diluted with ethyl acetate and then it was washed with brine. The organic layer was dried over Na₂SO₄, filtered and concentrated under reduced pressure and purified via flash chromatography using ethyl acetate and methanol as eluents to obtain ethyl (2R)-2-[5-[3,5-dichloro-2,6-dimethyl-4-[2-(4-methylpiperazin-1-yl)ethoxy]phenyl]-6-(4-fluorophenyl)thieno[2,3-d]pyrimidine-4-yl]oxy-3-[2-[[2-(2-methoxyphenyl)pyrimidin-4-yl]methoxy]phenyl]propanoate. MS: (M+H)=951.0

Step O (2R)-2-[5-[3,5-Dichloro-2,6-dimethyl-4-[2-(4-methylpiperazin-1-yl)ethoxy]phenyl]-6-(4-fluorophenyl)thieno[2,3-d]pyrimidin-4-yl]oxy-3-[2-[[2-(2-methoxyphenyl)pyrimidin-4-yl]methoxy]phenyl]propanoate acid 200 mg of compound of Step N above was dissolved in 5 mL dioxane-water 1:1 and 145 mg lithium hydroxide monohydrate (3.45 mmol) was added. The mixture was stirred at room temperature until no further conversion was observed. Then it was diluted with brine, neutralized 2M HCl, extracted with dichloromethane, dried over Na₂SO₄, filtered and concentrated under reduced pressure. The crude product was purified via preparative reversed phase chromatography using 1M aqueous NH₄HCO₃ solution and acetonitrile to obtain (2R)-2-[5-[3,5-dichloro-2,6-dimethyl-4-[2-(4-methylpiperazin-1-yl)ethoxy]phenyl]-6-(4-fluorophenyl)thieno[2,3-d]pyrimidin-4-yl]oxy-3-[2-[[2-(2-methoxyphenyl)pyrimidin-4-yl]methoxy]phenyl]propanoic acid. HRMS calculated for $C_{48}H_{45}N_6O_6FSCl_2$: 922.2482, found: 462.1310 (M+2H).

Step P (4-Methoxyphenyl)methyl (2R)-2-[5-[3,5-dichloro-2,6-dimethyl-4-[2-(4-methylpiperazin-1-yl)ethoxy]phenyl]-6-(4-fluorophenyl)thieno[2,3-d]pyrimidin-4-yl]oxy-3-[2-[[2-(2-methoxyphenyl)pyrimidin-4-yl]methoxy]phenyl]propanoate 400 mg compound of Step O above (0.433 mmol, 1 eq.), 341 mg triphenylphosphine (1.30 mmol, 3.0 eq.) and 180 mg 4-methoxybenzyl alcohol (1.30 mmol, 3.0 eq.) were dissolved in 5 mL dry toluene, then 300 mg di(tert)butyl azodicarboxylate (1.30 mmol, 3.0 eq.) was added in one portion. The resulting mixture was stirred at 50° C. until no further conversion was observed. The reaction mixture was concentrated, the crude product was purified by flash chromatography using dichloromethane/methanol (containing 1.2% $NH_3$) as eluent to obtain (4-methoxyphenyl)methyl (2R)-2-[5-[3,5-dichloro-2,6-dimethyl-4-[2-(4-methylpiperazin-1-yl)ethoxy]phenyl]-6-(4-fluorophenyl)thieno[2,3-d]pyrimidin-4-yl]oxy-3-[2-[[2-(2-methoxyphenyl)pyrimidin-4-yl]methoxy]phenyl]propanoate. MS: (M+H)=1043.2

Step Q

Benzyl {4-[2-[2,6-dichloro-4-{6-(4-fluorophenyl)-4-[(1R)-2-[(4-methoxyphenyl)methoxy]-1-[[2-[[2-(2-methoxyphenyl)pyrimidin-4-yl]methoxy]phenyl]methyl]-2-oxo-ethoxy]thieno[2,3-d]pyrimidin-5-yl]-3,5-dimethyl-phenoxy]ethyl}-1-methyl-piperazin-1-ium-1-yl}methyl phosphate 428 mg compound of Step P above (0.62 mmol, 1.5 eq.) were stirred in 4 mL dry acetonitrile at 40° C. until no further conversion was observed. The reaction mixture was injected directly onto a preconditioned 24 g silica column, then it was purified by flash chomatography using ethyl acetate/methanol (containing 1.2% $NH_3$) as eluent to give benzyl [4-[2-[2,6-dichloro-4-[6-(4-fluorophenyl)-4-[(1R)-2-[(4-methoxyphenyl)methoxy]-1-[[2-[[2-(2-methoxyphenyl)pyrimidin-4-yl]methoxy]phenyl]methyl]-2-oxo-ethoxy]thieno[2,3-d]pyrimidin-5-yl]-3,5-dimethyl-phenoxy]ethyl]-1-methyl-piperazin-1-ium-1-yl]methyl phosphate. MS: (M+H)=1243.2

Step R

Example 9

To the solution of 230 mg compound of Step P above (0.185 mmol) in 3 mL dichloromethane, 110 µL 33% HBr in acetic acid was added and it was stirred at 0° C. until no further conversion was observed. The reaction mixture was concentrated to dryness and the resulted product was purified by reversed phase chromatography using acetonitrile/25 mM $NH_4HCO_3$ as eluents. After lyophilization Example 9 was obtained as a white solid. HRMS calculated for $C_{49}H_{48}Cl_2FN_6O_{10}PS$: 1032.2251, found: 517.1213 (M+2H).

EXAMPLE 10

{4-[2-(4-{4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-3,5-dimethyl phenoxy)ethyl]-1-methylpiperazin-1-ium-1-yl}methyl hydrogen phosphate In the Example 10, the procedure is as in Example 1, using the appropriate chloride derivative of formula (IV) and the appropriate thienopyrimidine compound of formula (II).

EXAMPLE 11

{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl](dimethyl)ammonio}methyl hydrogen phosphate Step A 4-methoxybenzyl (2R)-2-{[(5S$_a$)-5-[3-chloro-4-[2-(dimethylamino)ethoxy]-2-methylphenyl-}-6-(4-fluorophenyl)thieno[2,3-d]pyrimidin-4-yl]oxy]-3-(2-[[2-(2-methoxyphenyl)pyrimidin-4-yl]methoxy] phenyl)propanoate 928 mg (2R)-2-{[(5S$_a$)-5-{3-chloro-4-[2-dimethylamino)ethoxy]-2-methylphenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoic acid (1.13 mmol, 1 eq.; synthesized according to WO 2015/097123), 889 mg triphenylphosphine (3.39 mmol, 3 eq.) and 468 mg 4-methoxybenzyl alcohol (3.39 mmol, 3 eq.) were dissolved in 12 mL dry toluene, then 781 mg di(tert)butyl azodicarboxylate (3.39 mmol, 3 eq.) was added in one portion. The resulting mixture was stirred at 50° C. until no further conversion was observed. The reaction mixture was concentrated and the crude product was purified by flash chromatography using ethyl acetate/methanol (containing 1.2% $NH_3$) as eluent. Product of Step A was obtained as off-white crystals. HRMS calculated for $C_{52}H_{47}ClFN_5O_7S$: 939.2869; found 4711.6511 (M+2H).

Step B

Benzyl [(2-[2-chloro-4-[6-(4-fluorophenyl)-4-{[(2R)-1{(4-methoxybenzyl)oxy]-3-(2-{[2-(2-methoxyphenyl)pyrimidin-4-yl]methoxy}phenyl)-1-oxopropan-2-yl]oxy}-(5S$_a$)-thieno[2,3-d]pyrimidin-5-yl]-3-methylphenoxy}ethyl)(dimethyl)ammonio] methyl phosphate 282 mg compound of Step A above (0.300 mmol, 1 eq.) and 147 mg dibenzyl chloromethyl phosphate (0.450 mmol, 1.5 eq.) were stirred in 1.5 mL dry acetonitrile at 40° C. until no further conversion was observed. The reaction mixture was injected directly onto a preconditioned 24 g silica column, then it was purified by flash chomatography using ethyl acetate/methanol (containing 1.2% $NH_3$) as eluent. Compound of Step B was obtained as off-white crystals. HRMS calculated for $C_{60}H_{56}ClFN_5O_{11}PS$: 1139.3107; found 570.6613 (M+2H).

Step C

Example 11

To the solution of 110 mg compound of Step B above (0.0964 mmol) in 1 mL dichloromethane, 175 µL 33% HBr in acetic acid was added and it was stirred at 0° C. until no further conversion was observed. The reaction mixture was concentrated, purified by flash chomatography using ethyl acetate/methanol (containing 1.2% $NH_3$) as eluent. Then the resulted product was purified by reversed phase chromatography using acetonitrile/5 mM $NH_4HCO_3$ as eluents. After lyophilization, Example 11 was obtained as a white solid. HRMS calculated for $C_{45}H_{42}BrClFN_5O_{10}PS$: 929.2062; found 465.6087 (M+2H).

In the following Examples 12 to 16, the procedure is as in Example 1, using the appropriate chloride derivative of formula (IV) and the appropriate thienopyrimidine compound of formula (II).

EXAMPLE 12

1-{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}ethyl hydrogen phosphate

EXAMPLE 13

1-{4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-yl}ethyl hydrogen phosphate

EXAMPLE 14

{1-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-4-methylpiperazin-1-ium-yl}methyl hydrogen phosphate

EXAMPLE 15

{1-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-4-methylpiperazin-1-ium-yl}ethyl hydrogen phosphate

EXAMPLE 16

{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-yl}methyl sulfate

EXAMPLE 17

1-[(acetyloxy)methyl]-4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl) thieno[2,3-d]pyrimidin-5-yl}-2-chloro-3-methylphenoxy)ethyl]-1-methylpiperazin-1-ium trifluoroacetate

Step A

1-[(acetyloxy)methyl]-4-(2-{2-chloro-4-[6-(4-fluorophenyl)-4-[[(2R)-1-[(4-methoxybenzyl)oxy]-3-(2-{[2-(2-methoxyphenyl)pyrimidin-4-yl]methoxy]phenyl)-1-oxopropan-2-yl]oxy}-(5S$_a$)-thieno[2,3-d]pyrimidin-5-yl]-3-methylphenoxy}ethyl)-1-methylpiperazin-1-ium trifluoroacetate To the solution of 149 mg compound obtained in Step A of Example 1 (0.150 mmol, 1 eq.) and 33 mg chloromethyl acetate (0.300 mmol, 2.0 eq.) in 2 mL dry acetonitrile, 22 mg sodium iodide (0.15 mmol, 1.0 eq.) was added and the reaction mixture was stirred at 70° C. until no further conversion was observed. The reaction mixture was purified by reversed phase chromatography using trifluoroacetic acid/acetonitrile (0.5 mL) and trifluoroacetic acid/H$_2$O (0.5 mL/L) as eluents. Product of Step A was obtained as trifluoroacetate salt. MS: M=1067.2

Step B

Example 17

To the solution of 73 mg compound of Step A above (0.062 mmol, 1 eq.) in 4 mL dichloromethane, 300 μL trifluoroacetic acid was added and the reaction mixture was stirred at room temperature until no further conversion was observed. The reaction mixture was evaporated to dryness then it was purified by reversed phase chromatography using trifluoroacetic acid/acetonitrile (0.5 mL/L) and trifluoroacetic acid/H$_2$O (0.5 mL/L) as eluents. After lyophilization, Example 17 was obtained as a white solid. HRMS calculated for $C_{50}H_{49}ClFN_6O_8S$: 947.3000; found 947.3001 (M).

EXAMPLE 18

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-{[(ethoxycarbonyl)oxy]methyl}-1-methylpiperazin-1-ium

Step A 4-(2-[2-chloro-4-[6-(4-fluorophenyl)-4-{[(2R)-1-[(4-methoxybenzyl)oxy]-3-(2-{[2-(2-methoxyphenyl)pyrimidin-4-yl]methoxy]phenyl)-1-oxopropan-2-yl]oxy}-(5S$_a$)-thieno[2,3-d]pyrimidin-5-yl]-3-methylphenoxy}ethyl)-1-{[(ethoxycarbonyl)oxy]methyl}-1-methylpiperazin-1-ium trifluoroacetate To the solution of 200 mg compound obtained in Step A of Example 1 (0.201 mmol, 1 eq.) and 56 mg ethyl chloromethyl carbonate (0.402 mmol, 2.0 eq.) in 2 mL dry acetonitrile, 30 mg sodium iodide (0.201 mmol, 1.0 eq.) was added and the reaction mixture was stirred at 70° C. until no further conversion was observed. The reaction mixture was purified by reversed phase chromatography using trifluoroacetic acid/acetonitrile (0.5 mL/L) and trifluoroacetic acid/H$_2$O (0.5 mL/L) as eluents. Compound of Step A was obtained as trifluoroacetate salt. HRMS calculated for $C_{59}H_{59}ClFN_6O_{10}S$: 1097.3680; found 1097.3694 (M).

Step B

Example 18

To the solution of 162 mg compound of Step A above (0.134 mmol, 1 eq.) in 4 mL dichloromethane, 300 μL trifluoroacetic acid was added and the reaction mixture was stirred at room temperature until no further conversion was observed. The reaction mixture was evaporated to dryness then it was purified by reversed phase chromatography using trifluoroacetic acid/acetonitrile (0.5 mL/L) and trifluoroacetic acid/H$_2$O (0.5 mL/L) as eluents. After lyophilization,

EXAMPLE 19

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-{[(diethylcarbamoyl)oxy]methyl}-1-methylpiperazin-1-ium trifluoroacetate

Step A 4-(2-[2-chloro-4-[6-(4-fluorophenyl)-4-{[(2R)-1-[(4-methoxybenzyl)oxy]-3-(2-{[2-(2-methoxyphenyl)pyrimidin-4-yl]methoxy}phenyl)-1-oxopropan-2-yl]oxy}-(5S$_a$)-thieno[2,3-d]pyrimidin-5-yl]-3-methylphenoxy]ethyl)-1-{[(diethylcarbamoyl)oxy]methyl}-1-methylpiperazin-1-ium trifluoroacetate To the solution of 200 mg compound obtained in Step A of Example 1 (0.201 mmol, 1 eq.) and 67 mg chloromethyl N,N-diethylcarbamate (0.402 mmol, 2.0 eq.) in 2 mL dry acetonitrile, 30 mg sodium iodide (0.201 mmol, 1.0 eq.) was added and the reaction mixture was stirred at 70° C. until no further conversion was observed. The reaction mixture was purified by reversed phase chromatography using trifluoroacetic acid acetonitrile (0.5 mL/L) and trifluoroacetic acid/H$_2$O (0.5 mL/L) as eluents. Compound of Step A was obtained as trifluoroacetate salt. HRMS calculated for C$_6$H$_{64}$ClFN$_7$O$_9$S: 1124.4153; found 1124.4209 (M).

Step B

Example 79

To the solution of 192 mg compound of stop A above (0.155 mmol, 1 eq.) in 4 mL dichloromethane, 300 µL trifluoroacetic acid was added and the reaction mixture was stirred at room temperature until no further conversion was observed. The reaction mixture was evaporated to dryness then it was purified by reversed phase chromatography using trifluoroacetic acid/acetonitrile (0.5 mL/L) and trifluoroacetic acid/H$_2$O (0.5 mL/L) as eluents. After lyophilization, Example 19 was obtained as a white solid. HRMS calculated for C$_{53}$H$_{56}$ClFN$_7$O$_8$S: 1004.3578; found 1004.3579 (M).

EXAMPLE 20

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-[(glycyloxy)methyl]-1-methylpiperazin-1-ium In the Example 20, the procedure is as in Example 1, using the appropriate chloride derivative of formula (IV) and the appropriate thienopyrimidine compound of formula (II). The obtained compound is quaternary ammonium salt in which counterions can be selected from bromide, chloride, iodide, acetate, trifluoroacetate, benzoate, mesylate, tosylate, triflate, or the like.

EXAMPLE 21

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-{1-[(diethylcarbamoyl)oxy]ethyl}-1-methylpiperazin-1-ium trifluoroacetate

Step A 1-chloroethyl N,N-diethylcarbamate

To the solution of 1.828 g diethylamine (25 mmol, 1.0 eq.) in tetrahydrofuran, 3.574 g 1-chloroethyl carbonochloridate (25 mmol, 1.0 eq.) was added dropwise at −78° C., then pyridine was added dropwise at −78° C. Reaction mixture as stirred at this temperature for 30 minutes, then it was let to warm to room temperature slowly (3 hours) and it was stirred overnight. The reaction mixture was concentrated, the crude product was diluted with 70 mL dichloromethane then it was washed with 50 mL 1N HCl aqueous then two times with 50 mL brine. Organic layer was dried over MgSO$_4$, it was filtered, the filtrate was concentrated under reduced pressure to give 1-chloroethyl N,N-diethylcarbamate as light brown oil, $^1$H NMR (400 MHz, CDCl$_3$): 6.64 (q, 1H), 3.34 (m, 4H), 1.83 (d, 3H), 1.17 (t, 6H).

Step B 4-(2-{2-chloro-4-[6-(4-fluorophenyl)-4-{[(2R)-1-[(4-methoxybenzyl)oxy]-3-(2-{[2-(2-methoxyphenyl)pyrimidin-4-yl]methoxy}phenyl)-1-oxopropan-2-yl]oxy}-(5S$_a$)-thieno[2,3-d]pyrimidin-5-yl]-3-methylphenoxy}ethyl)-1-{1-[(diethylcarbamoyl)oxy]ethyl}-1-methylpiperazin-1-ium trifluoroacetate To the solution of 250 mg compound obtained in Step A of Example 1 (0.251 mmol, 1.0 eq.) and 225 mg compound of Step A above (1.26 mmol, 5.0 eq.) in 5 mL acetonitrile, 75 mg sodium iodide (0.50 mmol, 2.0 eq.) was added and it was stirred at 45° C. for 45 minutes. The reaction mixture was cooled, filtered, then it was purified by reversed phase chromatography using trifluoroacetic acid/acetonitrile (0.5 mL/L) and trifluoroacetic acid/H$_2$O (0.5 mL/L) as eluents. Compounds of Step B were obtained as trifluoroacetate salts of the diastereomers (diastereomers were not separated). MS: M=1138.4

Step C

Example 21

To the solution of 81 mg compounds of Step B above (0.0647 mmol, 1 eq.) in 5 mL dichloromethane 800 µL trifluoroacetic acid was added and the reaction mixture was stirred at room temperature until no further conversion was observed. The reaction mixture was evaporated to dryness then it was purified by reversed phase chromatography using trifluoroacetic acid/acetonitrile (0.5 mL/L) and trifluoroacetic acid/H$_2$O (0.5 mL/L) as eluents. After lyophilization, Example 21 was obtained as a white solid (diastereomers were not separated). HRMS calculated for C$_{54}$H$_{58}$ClFN$_7$O$_8$S: 1018.3735; found 509.6925 (M+H)$^{2+}$.

EXAMPLE 22

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methyl-1-[(5-methyl-2-oxo-1,3-dioxol-4-yl)methyl]piperazin-1-ium trifluoroacetate

Step A 4-(2-{2-chloro-4-[6-(4-fluorophenyl)-4-{[(2R)-1-[(4-methoxybenzyl)oxy]-3-(2-{[2-(2-methoxyphenyl)pyrimidin-4-yl]methoxy}phenyl)-1-oxopropan-2-yl]oxy}-(5S$_a$)-thieno[2,3-d]pyrimidin-5-yl]-3-methylphenoxy}ethyl)-1-1-[(5-methyl-2-oxo-1,3-dioxol-4-yl)methyl]piperazin-1-ium trifluoroacetate To the solution of 348 mg compound obtained in Step A of Example 1 (0.350 mmol, 1 eq.) and 104 mg 4-(chloromethyl)-5-methyl-1,3-dioxol-2-one (0.700 mmol, 2.0 eq.) in 2 mL dry acetonitrile. 52 mg sodium iodide (0.35 mmol, 1.0 eq.) was added and the reaction mixture was stirred at 70° C. until no further conversion was observed. The reaction mixture was purified by reversed phase chromatography using trifluoroacetic acid/acetonitrile (0.5 mL/L) and trifluoroacetic acid/H$_2$O (0.5 mL/L) as eluents. Compound of Step A was obtained as trifluoroacetate salt. MS: M=1107.2

Step B

Example 22

To the solution of 250 mg compound of Step A above (0.205 mmol, 1 eq.) in 8 mL dichloromethane, 600 µL trifluoroacetic acid was added and the reaction mixture was stirred at room temperature until no further conversion was observed. The reaction mixture was evaporated to dryness then it was purified by reversed phase chromatography using trifluoroacetic acid/acetonitrile (0.5 mL/L) and trifluoroacetic acid/H$_2$O (0.5 mL/L) as eluents. After lyophilization, Example 22 was obtained as a white solid. HRMS calculated for C$_2$H$_{49}$ClFN$_6$O$_9$S: 987.2949; found 987.2961 (M).

EXAMPLE 23

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methyl-1-[(L-valyloxy)methyl]piperazin-1-ium In the Example 23, the procedure is as in Example 1, using the appropriate chloride derivative of formula (IV) and the appropriate thienopyrimidine compound of formula (II). The obtained compound is a quaternary ammonium salt which counterions can be selected from bromide, chloride, iodide acetate, trifluoroacetate benzoate, mesylate, tosylate triflate, or the like.

EXAMPLE 24

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-{[(2,2-dimethylpropanoyl)oxy]methyl}-1-methylpiperazin-1-ium trifluoroacetate

Step A 4-(2-{2-chloro-4-[6-(4-fluorophenyl)-4-{[(2R)-1-[(4-methoxybenzyl)oxy]-3-(2-[[2-(2-methoxyphenyl)pyrimidin-4-yl]methoxy}phenyl)-1-oxopropan-2-yl]oxy}-(5S$_a$)-thieno[2,3-d]pyrimidin-5-yl]-3-methylphenoxy]ethyl)-1-{[(2,2-dimethylpropanoyl)oxy]methyl}1-methylpiperazin-1-ium trifluoroacetate To the solution 249 mg compound obtained in Step A of Example 1 (0.250 mmol, 1 eq.) and 75 mg chloromethyl 2,2-dimethylpropanoate (0.500 mmol, 2.0 eq.) in 2 mL, dry acetonitrile, 37 mg sodium iodide (0.25 mmol, 1.0 eq.) was added and the reaction mixture was stirred a 70° C. until no further conversion was observed. The reaction mixture was purified by reversed phase chromatograph using trifluoroacetic acid/acetonitrile (0.5 mL/L) and trifluoroacetic acid/H$_2$O (0.5 mL/L) as eluents. Compound of Step A was obtained as trifluoroacetate salt. HRMS calculate for C$_{61}$H$_{62}$ClFN$_6$O$_9$S: 1109.4044; found 1109.4040 (M).

Step B

Example 24

To the solution of 216 mg compound of Step A above (0.177 mmol, 1 eq.) in 8 mL dichloromethane, 600 µL trifluoroacetic acid was added and the reaction mixture was stirred at room temperature until no further conversion was observed. The reaction mixture was evaporated to dryness then it was purified by reversed phase chromatography using trifluoroacetic acid/acetonitrile (0.5 mL/L) and trifluoroacetic acid/H$_2$O (0.5 mL/L) as eluents. After lyophilization, Example 24 was obtained as a white solid. HRMS calculated for C$_{53}$H$_{55}$ClFN$_6$O$_8$S: 989.3469; found 989.3480 (M).

EXAMPLE 25

1-[(acetyloxy)methyl]-4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl) thieno[2,3-d]pyrimidin-5-yl}-2-chlorophenoxy)ethyl]-1-methylpiperazin-1-ium trifluoroacetate

Step A

1-[(acetyloxy)methyl]-4-(2-{3-bromo-2-chloro-4-[6-(4-fluorophenyl)-4-{[(2R)-1-[(4-methoxybenzyl)oxy]-3-(2-{[2-(2-methoxyphenyl)pyrimidin-4-yl]methoxy}phenyl)-1-oxopropan-2-yl]oxy}-(5S$_a$)-thieno[2,3-d]pyrimidin-5-yl]phenoxy}ethyl)-1-methylpiperazin-1-ium trifluoroacetate To the solution of 212 mg compound obtained in Step A of Example 5 (0.20 mmol, 1 eq.) to and 43 mg chloromethyl acetate (0.40 mmol, 2.0 eq.) in 2 mL dry acetonitrile, 30 mg sodium iodide (0.20 mmol, 1.0 eq.) was added and the reaction mixture was stirred at 70° C. until no further conversion was observed. The reaction mixture was purified by reversed phase chromatography using trifluoroacetic acid/acetonitrile (0.5 mL/L) and trifluoroacetic acid/H$_2$O (0.5 mL/L) as eluents. Compound of Step A was obtained as trifluoroacetate salt. MS: M=1131.0

Step B

Example 25

To the solution of 105 mg compound of Step A above (0.842 mmol, 1 eq.) in 4 mL dichloromethane, 300 µL trifluoroacetic acid was added and the reaction mixture was stirred at room temperature until no further conversion was observed. The reaction mixture was evaporated to dryness then it was purified by reversed phase chromatograph using trifluoroacetic acid/acetonitrile (0.5 mL/L) and trifluoroacetic acid/H$_2$O (0.5 as eluents. After lyophilization, Example 25 was obtained as a white solid. HRMS calculated for C$_{49}$H$_{46}$BrClFN$_6$O$_8$S: 1011.1948; found 1011.1949 (M).

EXAMPLE 26

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-{[(ethoxycarbonyl)oxy]methyl}-1-methylpiperazin-1-ium trifluoroacetate Step A 4-(2-[3-bromo-2-chloro-4-[6-(4-fluorophenyl)-4-{[(2R)-1-[(4-methoxybenzyl)oxy]-3-(2-{[2-(2-methoxyphenyl)pyrimidin-4-yl]methoxy]phenyl)-1-oxopropan-2-yl]oxy}-(5S$_a$)-thieno[2,3-d]pyrimidin-5-yl]phenoxy}ethyl-1-{[(ethoxycarbonyl)oxy]methyl}-1-methylpiperazin-1-ium trifluoroacetate To the solution of 252 mg compound obtained in Step A of Example 5 (0.20 mmol, 1 eq.) and 55 mg ethyl chloromethyl carbonate (0.40 mmol, 2.0 eq.) in 2 mL dry acetonitrile, 30 mg sodium iodide (0.20 mmol, 1.0 eq.) was added and the reaction mixture was stirred at 70° C. until no further conversion was observed. The reaction mixture was purified by reversed phase chromatography using trifluoroacetic acid/acetonitrile (0.5 mL/L) and trifluoroacetic acid/H$_2$O (0.5 mL/L) eluents. Compound of Step A was obtained as trifluoroacetate salt. HRMS calculated for C$_{58}$H$_{56}$BrClFN$_6$O$_{10}$S: 1161.2629 found 1161.2674 (M).

Step B

Example 26

To the solution of 140 mg compound of Step A above (0.188 mmol, 1 eq.) in 4 mL dichloromethane, 300 µL trifluoroacetic acid was added and the reaction mixture was stirred at room temperature until no further conversion was observed. The reaction mixture was evaporated to dryness then it was purified by reversed phase chromatography using trifluoroacetic acid/acetonitrile (0.5 mL/L) and trifluoroacetic acid/H$_2$O (0.5 mL/L) as eluents. After lyophilization, Example 26 was obtained as a white solid. HRMS calculated for C$_{50}$H$_{48}$BrClFN$_6$O$_9$S: 1041.2054; found 1041.2049 (M).

EXAMPLE 27

1-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-{[(diethylcarbamoyl)oxy]methyl}-1-methylpiperazin-1-ium trifluoroacetate Step A 4-(2-[3-bromo-2-chloro-4-[6-(4-fluorophenyl)-4-{[(2R)-1-[(4-methoxybenzyl)oxy]-3-(2-{[2-(2-methoxyphenyl)pyrimidin-4-yl]methoxy]phenyl)-1-oxopropan-2-yl]oxy}-(5S$_a$)-thieno[2,3-d]pyrimidin-5-yl]phenoxy}ethyl-1-{[(diethylcarbamoyl)oxy]methyl}-1-methylpiperazin-1-ium trifluoroacetate To the solution of 212 mg compound obtained in Step A of Example 5 (0.20 mmol, 1 eq.) and 66 mg chloromethyl N,N-diethylcarbamate (0.40 mmol, 2.0 eq.) in 2 mL dry acetonitrile, 30 mg sodium iodide (0.20 mmol, 1.0 eq.) was added and the reaction mixture was stirred at 70° C. until no further conversion was observed. The reaction mixture was purified by reversed phase chromatography using trifluoroacetic acid/acetonitrile (0.5 mL/L) and trifluoroacetic acid/H$_2$O (0.5 mL/L) as eluents. Compound of Step A was obtained as trifluoroacetate salt. HRMS calculated for C$_{60}$H$_{61}$BrClFN$_7$O$_9$S: 1188.3102; found 1188.3101 (M).

Step B

Example 27

To the solution of 208 mg compound of Step A above (0.160 mmol, 1 eq.) in 4 mL dichloromethane, 300 µL trifluoroacetic acid was added and the reaction mixture was stirred at room temperature until no further conversion was observed. The reaction mixture was evaporated to dryness then it was purified by reversed phase chromatography using trifluoroacetic acid/acetonitrile (0.5 mL/L) and trifluoroacetic acid/H$_2$O (0.5 mL/L) as eluents. After lyophilization, Example 27 was obtained as a white solid, HRMS calculated for C$_{52}$H$_{53}$BrClFN$_7$O$_8$S: 1068.2527; found 1068.2514 (M).

EXAMPLE 28

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-[(glycyloxy)methyl]-1-methylpiperazin-1-ium In the Example 28, the procedure is as in Example 1, using the appropriate chloride derivative of formula (IV) and the appropriate thienopyrimidine compound of formula (II). The obtained compound is a quaternary ammonium salt in which counterions can be selected from bromide, chloride, iodide, acetate, trifluoroacetate, benzoate, mesylate, tosylate, triflate, or the like.

EXAMPLE 29

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-{1-[(diethylcarbamoyl)oxy]ethyl}-1-methylpiperazin-1-ium trifluoroacetate

Step A 4-(2-[3-bromo-2-chloro-4-[6-(4-fluorophenyl)-4-{[(2R)-1-[(4-methoxybenzyl)oxy]-3-(2-{[2-(2-methoxyphenyl)pyrimidin-4-yl]methoxy]phenyl)-1-oxopropan-2-yl]oxy}-(5S$_a$)-thieno[2,3-d]pyrimidin-5-yl]phenoxy}ethyl-1-{[(diethylcarbamoyl)oxy]}-1-methylpiperazin-1-ium trifluoroacetate To the solution of 250 mg compound obtained in Step A of Example 5 (0.236 mmol, 1.0 eq.) and 212 mg compound obtained in Step A of Example 21 (1.18 mmol, 5.0 eq.) in 5 mL acetonitrile, 71 mg sodium iodide (0.471 mmol, 2.0 eq.) was added and it was stirred at 45° C. for 45 minutes. The reaction mixture was cooled, filtered, then it was purified by reversed phase chromatography using trifluoroacetic acid/acetonitrile (0.5 mL/L) and trifluoroacetic acid/H$_2$O (0.5 mL/L) as eluents. Compounds of Step A were obtained as trifluoroacetate salts of the diastereomers (diastereomers were not separated). MS: (M+H)$^{2+}$=602.8

Step B

Example 29

To the solution of 51 mg compounds of Step A above (0.0387 mmol, 1 eq.) in 5 mL dichloromethane, 800 μL trifluoroacetic acid was added and the reaction mixture was stirred at room temperature until no further conversion was observed. The reaction mixture was evaporated to dryness then it was purified by reversed phase chromatography using trifluoroacetic acid/acetonitrile (0.5 mL/L) and trifluoroacetic acid/H$_2$O (0.5 mL/L) as eluents. After lyophilization, Example 29 was obtained as a white solid (diastereomers were not separated). HRMS calculated for C$_{53}$H$_{55}$BrClFN$_7$O$_8$S: 1082.2683; found 541.6396 (M+H)$^{2+}$ and 541.6389 (M+H)$^{2+}$.

EXAMPLE 30

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methyl-1-[(5-methyl-2-oxo-1,3-dioxol-4-yl)methyl]piperazin-1-ium trifluoroacetate

Step A 4-(2-[3-bromo-2-chloro-4-[6-(4-fluorophenyl)-4-{[(2R)-1-[(4-methoxybenzyl)oxy]-3-(2-{[2-(2-methoxyphenyl)pyrimidin-4-yl]methoxy]phenyl)-1-oxopropan-2-yl]oxy}-(5S$_a$)-thieno[2,3-d]pyrimidin-5-yl]phenoxy}ethyl-1-[5-methyl-2-oxo-1,3-dioxol-4-yl)methyl]piperazin-1-ium trifluoroacetate To the solution of 212 mg compound obtained in Step A of Example 5 (0.200 mmol, 1 eq.) and 59 mg 4-(chloromethyl)-5-methyl-1,3-dioxol-2-one (0.40 mmol, 2.0 eq.) in 2 mL dry acetonitrile, 30 mg sodium iodide (0.20 mmol, 1.0 eq.) was added and the reaction mixture was stirred at 70° C. until no further conversion was observed. The reaction mixture was purified by reversed phase chromatography using trifluoroacetic acid/acetonitrile (0.5 mL/L) and trifluoroacetic acid/H$_2$O (0.5 mL/L) as eluents. Compound of Step A was obtained as trifluoroacetate salt. HRMS calculated for C$_{59}$H$_{54}$BrClFN$_6$O$_{10}$S: 1171.2473; found 1171.2461 (M).

Step B

Example 30

To the solution of 225 mg compound of Step A above (0.175 mmol, 1 eq.) in 8 mL dichloromethane, 600 μL trifluoroacetic acid was added and the reaction mixture was stirred at room temperature until no further conversion was observed. The reaction mixture was evaporated to dryness then it was purified by reversed phase chromatography using trifluoroacetic acid/acetonitrile (0.5 mL/L) and trifluoroacetic acid/H$_2$O (0.5 mL/L) as eluents. After lyophilization, Example 30 was obtained as a white solid. HRMS calculated for C$_{51}$H$_{46}$BrClFN$_6$O$_9$S: 1051.1897; found 1051.1891 (M).

EXAMPLE 31

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methyl-1-[(L-valyloxy)methyl]piperazin-1-ium In the Example 31, the procedure is as in Example 1, using the appropriate chloride derivative of formula (IV) and the appropriate thienopyrimidine compound of formula (II). The obtained compound is a quaternary ammonium salt in which counterions can be selected from bromide, chloride, iodide, acetate, trifluoroacetate, benzoate, mesylate, tosylate, triflate, or the like.

EXAMPLE 32

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-{[(2,2-dimethylpropanoyl)oxy]methyl}-1-1-methyl piperazin-1-ium trifluoroacetate

Step A 4-(2-[3-bromo-2-chloro-4-[6-(4-fluorophenyl)-4-{[(2R)-1-[(4-methoxybenzyl)oxy]-3-(2-{[2-(2-methoxyphenyl)pyrimidin-4-yl]methoxy]phenyl)-1-oxopropan-2-yl]oxy}-(5S$_a$)-thieno[2,3-d]pyrimidin-5-yl]phenoxy}ethyl-1-{[(2,2-dimethylpropanoyl)oxy]methyl}-1-methylpiperazin-1-ium trifluoroacetate To the solution of 212 mg compound obtained in Step A of Example 5 (0.200 mmol, 1 eq.) and (60 mg chloromethyl 2,2-dimethylpropanoate (0.40 mmol, 2.0 eq.) in 2 mL dry acetonitrile, 30 mg sodium iodide (0.20 mmol, 1.0 eq.) was added and the reaction mixture was stirred at 70° C. until no further conversion was observed. The reaction mixture was purified by reversed phase chromatography using trifluoroacetic acid/acetonitrile (0.5 mL/L) and trifluoroacetic acid/H$_2$O (0.5 mL/L) as eluents. Compound of Step A was obtained as trifluoroacetate salt. HRMS calculated for C$_{60}$H$_{60}$BrClFN$_6$O$_9$S: 1173.2993; found 1173.2994 (M).

Step B

Example 32

To the solution of 115 mg compound of Step A above (0.167 mmol, 1 eq.) in 8 mL dichloromethane, 600 μL trifluoroacetic acid was added and the reaction mixture was stirred at room temperature until no further conversion was observed. The reaction mixture was evaporated to dryness then it was purified by reversed phase chromatography using trifluoroacetic acid/acetonitrile (0.5 mL/L) and trifluoroacetic acid/H$_2$O (0.5 mL/l) as eluents. After lyophilization, Example 32 was obtained as a white solid. HRMS calculated for C$_{52}$H$_{52}$BrClFN$_6$O$_8$S: 1053.2418; found 1053.2405 (M).

Depending on their electronic charge and the pH in solution, Examples 1, 4, 5 and 8 to 15 can exist as four ionic forms (zwitterionic, dianionic, anionic or cationic); Examples 2, 3, 6 and 7 can exist as three forms (zwitterionic, anionic or cationic); and Examples 1 to 32 can exist as two forms (zwitterionic or cationic).

Example A: Inhibition of Mcl-1 by the Fluoroscence Polarisation Technique

The relative, binding potency of each compound was determined via Fluorescence Polarisation (FP). The method utilised a Fluorescein labelled ligand (Fluorescein-βAla-Ahx-A-REIGAQLRRMADDLNAQY-OH; mw 2,765) which binds to the Mcl-1 protein (such that Mcl-1 corresponds to the UniProtKB® primary accession number: Q07820) leading to an increased anisotropy measured in milli-polarisation (mP) units using a reader. The addition of a compound which binds competitively to the same site as the ligand will result in a greater proportion of unbound ligand in the system indicated by a decrease in mP units.

An 11 point serial dilution of each compound was prepared in DMSO and 2 μl transferred into flat bottomed, low binding, 384-well plate (final DMSO concentration 5%), 38 μl of buffer (10 mM 4-(2-hydroxyethyl)-1-piperazineethanesolfonic acid [HEPES], 150 mM NaCl, 0.05% Tween 20, pH 7.4), containing the Fluorescein labelled ligand (final concentration 1 nM) and Mcl-1 protein (final concentration 5 nM) was then added.

Assay plates were incubated ~2 hours at room temperature before FP was measured on a Biomek Synergy2 reader (Ex. 528 nm, Em. 640 nm, Cut off 510 nm) and mP units calculated. The binding of increasing doses of test compound was expressed as a percentage reduction in mP compared to a window established between '5% DMSO only' and '100% inhibition' controls. 11-point dose response curves were plotted with XL-Fit software using a 4-Parameter Logistic Model (Sigmoidal Dose-Response Model) and the inhibitory concentrations that gave a 50% reduction in mP (IC$_{50}$) were determined. Results are presented in Table 1 below.

The results show that the compounds of the invention inhibit interaction between the Mcl-1 protein and the fluorescent peptide described hereinbefore.

Example B: In Vitro Cytotoxicity

The cytotoxicity studies were carried out on the H929 multiple myeloma tumour line.

The cells are distributed onto microplates and exposed to the test compound for 48 hours.

The cell viability is then quantified by a colorimetric assay, the Microculture Tetrazolium Assay (Carmichael et al. Cancer Res. 1987, 47, 936-942).

The results are expressed in IC$_{50}$ (the concentration of compound that inhibits cell viability by 50%) and are presented in Table 1 below.

The results show that the compounds of the invention are cytotoxic.

TABLE 1

IC$_{50}$ of Mcl-1 inhibition (fluorescence polarisation test) and of cytotoxicity for H929 cells

| | IC$_{50}$ (M) Mcl-LFP | IC$_{50}$ (M) MTT H929 |
|---|---|---|
| Example 1 | 1.03E-09 | 2.84E-08 |
| Example 2 | 9.48E-10 | 1.09E-08 |
| Example 3 | ND | ND |
| Example 4 | ND | ND |
| Example 5 | 1.06E-09 | 5.54E-08 |
| Example 6 | ND | ND |
| Example 7 | ND | ND |
| Example 8 | 9.48E-10 | 2.29E-07 |
| Example 9 | ND | ND |
| Example 10 | ND | ND |
| Example 11 | 1.06E-09 | 3.93E-08 |
| Example 12 | ND | ND |
| Example 13 | ND | ND |
| Example 14 | ND | ND |
| Example 15 | ND | ND |
| Example 16 | ND | ND |
| Example 17 | 1.12E-09 | 2.15E-09 |
| Example 18 | 9.48E-10 | 1.74E-09 |
| Example 19 | 1.2E-09 | 1.64E-06 |
| Example 20 | ND | ND |
| Example 21 | 1.96E-09 | 7.04E-08 |
| Example 22 | 9.48E-10 | 2.23E-09 |
| Example 23 | ND | ND |
| Example 24 | 1.04E-09 | 2.52E-09 |
| Example 25 | 1.07E-09 | 1.95E-09 |
| Example 26 | 9.48E-10 | 2.29E-09 |
| Example 27 | 1.17E-09 | 1.9E-06 |
| Example 28 | ND | ND |
| Example 29 | 1.36E-09 | 1.36E-07 |
| Example 30 | 9.48E-10 | 2.81E-09 |
| Example 31 | ND | ND |
| Example 32 | 1.77E-09 | 2.11E-09 |

ND: not determined

Example C: Quantification of the Cleaved Form of PARP In Vivo

The ability of the compounds of the invention to induce apoptosis, by measuring cleaved PARP levels, is evaluated in a xenograft model of AMO-1 multiple myeloma cells, 5.10$^6$ AMO-1 cells are grafted sub-cutaneously into inummosuppressed mice (SCID) strain), 12 to 14 days after the graft, the animals are treated by intravenous routes with the various compounds. After treatment, the tumour masses are recovered and lysed, and the cleaved form of PARP is quantified in the tumour lysates.

The quantification is carried out using the "Meso Scale Discovery (MSD) ELISA platform" tests, which specifically assays the cleaved form of PARP. It is expressed in the form of an activation factor corresponding to the ratio between the quantity of cleaved PARP in the tumors from treated mice divided by the quantity of cleaved PARP in the tumors from untreated mice.

The results show that the compounds of the invention are capable of inducing apoptosis in AMO-1 tumour cells in vivo.

Example D: Anti-Tumour Activity In Vivo

The anti-tumour activity of the compounds of the invention is evaluated in a xenograft model of AMO-1 multiple myeloma cells.

$1 \times 10^7$ AMO-1 cells are grafted sub-cutaneously into immunosuppressed mice (SCID strain). 6 to 8 days after the graft, when the tumour mass has reached about 150 mm$^3$, the mice are treated with the various compounds in a daily schedule (5-day treatment). The tumour mass is measured twice weekly from the start of treatment.

The results obtained using $\Delta T/C$ ratio (i.e. qualification parameter of the activity of a product, which is defined as the ratio tumour volume of the treated group tumour volume of the untreated control group) show that the compounds of the invention induce a prolonged and significant complete tumour regression after the treatment period.

Example E: Solubility Test

Method 1:

Sample solutions (around 16.7 mg/ml) in propylene glycol were diluted with water (30% propylene glycol). Then, samples were shaked for 72 hours at room temperature. After shaking period, samples were centrifuged, then the liquid phase was filtered and analyzed using HPLC coupled to UV detection. To determine the actual concentration a 5-point calibration curve was established.

For instance, in these conditions, the solubility of the compound of Example 1 was significantly increased (≥4907 µM) compared to (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid (63.3 µM) disclosed in WO 2015/097123.

Method 2:

Samples (40 mg/mL) were diluted in aqueous phosphate buffer (67.7 mM, with pH adjusted at 7.4) used for in vivo studies. Samples were shaked at room temperature, then filtered. The solubilized fraction was quantified by LC-MS-MS analysis.

In these conditions, compounds of Example 1 and Example 11 showed high solubility (>35 mg/mL) which are more soluble compared to (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoic acid and (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoic acid, respectively, disclosed in WO 2015/097123.

Example F: Pharmaceutical Composition: Tablets

| | |
|---|---|
| 1000 tablets containing a dose of 5 mg of a compound selected from Examples 1 to 32 | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:

1. A compound of formula (I):

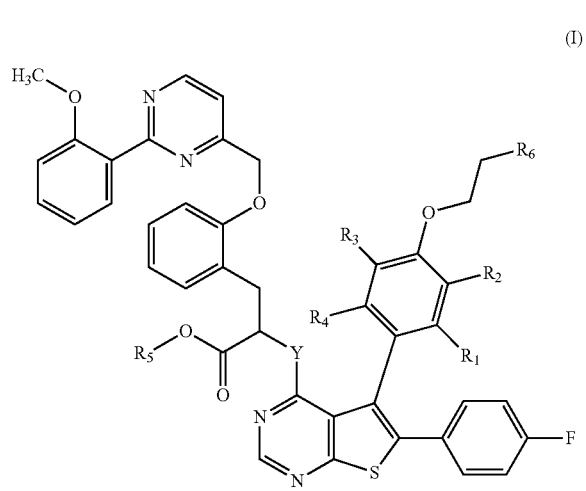

wherein:
Y represents a —NH— group or an oxygen atom;
R$_1$ represents a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)alkoxy group, a —S—(C$_1$-C$_6$)alkyl group, a linear or branched (C$_1$-C$_6$)polyhaloalkyl group, a hydroxy group, a hydroxy(C$_1$-C$_6$)alkyl group, a cyano group, —NR$_9$R$_9$', —Cy$_1$ or a halogen atom;
R$_2$, R$_3$ and R$_4$ independently of one another represent a hydrogen atom, a halogen atom, a linear or branched (C$_1$-C$_6$)alkyl group, a linear or branched (C$_2$-C$_6$) alkenyl group, a linear or branched (C$_2$-C$_6$)alkynyl group, a linear or branched (C$_1$-C$_6$)polyhaloalkyl, a hydroxy group, a hydroxy(C$_1$-C$_6$)alkyl group, a linear or branched (C$_1$-C$_6$)alkoxy group, a —S—(C$_1$-C$_6$)alkyl group, a cyano group, a nitro group, -alkyl(C$_0$-C$_6$)—NR$_9$R$_9$', —O-alkyl(C$_1$-C$_6$)—NR$_9$R$_9$', —C(O)—OR$_9$, —O—C(O)—R$_9$, —C(O)—NR$_9$R$_9$', —NR$_9$—C(O)—R$_9$', —NR$_9$—C(O)—OR$_9$', -alkyl (C$_1$-C$_6$)—NR$_9$—C(O)—R$_9$', —SO$_2$—NR$_9$R$_9$', or —SO$_2$-alkyl(C$_1$-C$_6$);
R$_5$ represents a hydrogen atom;
R$_6$ represents the group

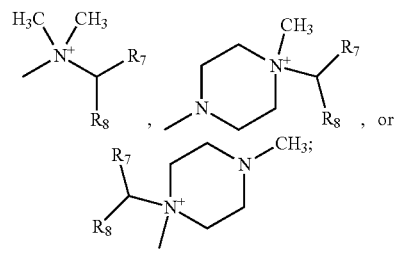

R$_7$ represents a hydrogen atom or a linear or branched (C$_1$-C$_6$)alkyl group;

R$_8$ represents a —O—P(O)(O$^-$)(O$^-$) group, a —O—P(O)(O$^-$)(OR$_{10}$) group, a —O—P(O)(OR$_{10}$)(OR$_{10}$') group, a —O—SO$_2$—O$^-$ group, a —O—SO$_2$—OR$_{10}$ group, —Cy$_2$, a —O—C(O)—R$_9$ group, a —O—C(O)—OR, group or a —O—C(O)—NR$_9$R$_9$' group;

R$_9$ and R$_9$' independently of one another represent a hydrogen atom, a linear or branched (C$_1$-C$_6$)alkyl group or a linear or branched amino(C$_1$-C$_6$)alkyl group;

R$_{10}$ and R$_{10}$' independently of one another represent a hydrogen atom, a linear or branched (C$_1$-C$_6$)alkyl group or an arylalkyl(C$_1$-C$_6$) group;

Cy$_1$ and Cy$_2$ independently of one another, represent a cycloalkyl group, a heterocycloalkyl group, an aryl group or a heteroaryl group;

wherein the ammonium so defined may exist as a zwitterionic form or may have a monovalent anionic counterion, and wherein:
"aryl" means a phenyl or naphthyl group,
"heteroaryl" means any mono- or bi-cyclic group composed of from 5 to 10 ring members, having at least one aromatic moiety and having from 1 to 3 heteroatoms selected from oxygen, sulphur and nitrogen,
"cycloalkyl" means any mono- or bi-cyclic non-aromatic carbocyclic group having from 3 to 10 ring members,
"heterocycloalkyl" means any mono- or bi-cyclic non-aromatic carbocyclic group having from 3 to 10 ring members, and having from 1 to 3 heteroatoms selected from oxygen, sulphur and nitrogen, which may have fused, bridged or spiro ring systems, wherein the aryl, heteroaryl, cycloalkyl and heterocycloalkyl groups so defined and the alkyl, alkenyl, alkynyl, alkoxy groups, to be substituted by from 1 to 4 groups selected from linear or branched (C$_1$-C$_6$)alkyl, linear or branched (C$_2$-C$_6$)alkenyl group, linear or branched (C$_2$-C$_6$)alkynyl group, linear or branched (C$_1$-C$_6$)alkoxy, (C$_1$-C$_6$)alkyl-S—, hydroxy, oxo (or N-oxide where appropriate), nitro, cyano, —C(O)—OR', —O—C(O)—R', —C(O)—NR'R'', —NR'R'', —(C=NR')—OR'', linear or branched (C$_1$-C$_6$)polyhaloalkyl, trifluoromethoxy or halogen, wherein R' and R'' independently of one another represent a hydrogen atom or a linear or branched (C$_1$-C$_6$)alkyl group, and wherein one or more of the carbon atoms of the preceding possible substituents, may be deuterated, its enantiomers, diastereoisomers and atropisomers, and addition salts thereof with a pharmaceutically acceptable acid or base.

2. The compound according to claim 1, wherein Y represents an oxygen atom.

3. The compound according to claim 1, wherein at least one of the groups selected from R$_2$, R$_3$ and R$_4$ does not represent a hydrogen atom.

4. The compound according to claim 1, wherein R$_1$ represents a linear or branched (C$_1$-C$_6$)alkyl group or a halogen atom.

5. The compound according to claim 1, wherein R$_2$ represents a halogen atom, a hydroxy group, or a linear or branched (C$_1$-C$_6$)alkoxy group.

6. The compound according to claim 1, wherein R$_3$ and R$_4$ represent a hydrogen atom.

7. The compound according to claim 1, wherein the substituents of the pair (R$_1$, R$_4$) are identical and the substituents of the pair (R$_2$, R$_3$) are identical.

8. The compound according to claim 1, wherein R$_6$ represents

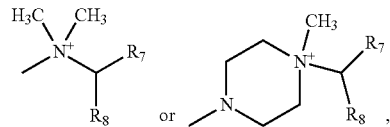

wherein R$_7$ and R$_8$ are as defined in claim 1.

9. The compound according to claim 1, wherein R$_6$ represents

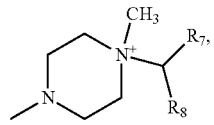

wherein R$_7$ and R$_8$ are as defined in claim 1.

10. The compound according to claim 1, wherein R$_7$ represents a methyl group or a hydrogen atom.

11. The compound according to claim 1, wherein R$_8$ represents a —O—P(O)(O$^-$)(OR$_{10}$) group in which R$_{10}$ represents a hydrogen atom, a benzyl group or a methyl group.

12. The compound according to claim 1, wherein R$_8$ represents a 5-methyl-2-oxo-1,3-dioxol-4-yl group; a —O—C(O)—CH$_3$ group; a —O—C(O)-tBu group; a —O—C(O)—CH$_2$—NH$_2$ group; a —O—C(O)—CH[CH(CH$_3$)$_2$]—NH$_2$ group; a —O—C(O)—O—CH$_2$CH$_3$ group; or a —O—C(O)—N(CH$_2$CH$_3$)$_2$ group.

13. The compound according to claim 1, which is selected from the group consisting of:

{4-[2-(4-{(5S$_a$)-4-(1R)-1-carboxy-2-(2-{[2-{[(2-methoxyphenyl)pyrimidin-4-yl]methoxy}phenyl)ethoxy]-6-4-fluorophenyl)thieno[2,3-d]pyrimidin-5-yl}-2-chloro-3-methylphenoxy)ethyl]-1-methylpiperazin-1-ium-1-yl}methyl hydrogen phosphate;

benzyl {4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl phosphate;

{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl methyl phosphate;

{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-ethylphenoxy)ethyl]-1-methylpiperazin-1-ium-1-yl}methyl hydrogen phosphate;

{4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}methyl hydrogen phosphate;

benzyl {4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}methyl phosphate;

{4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}methyl methyl phosphate;

N-[(5S$_a$)-5-{3-chloro-4-[2-(4-{[(hydroxyphosphinato)oxy]methyl}-4-methylpiperazin-4-ium-1-yl)ethoxy]-2-methylphenyl}-6-(4-fluorophenyl)thieno[2,3-d]pyrimidin-4-yl]-2-{[2-(2-methoxyphenyl)pyrimidin-4-yl]methoxy}-D-phenylalanine;

{4-[2-(4-{4-(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2,6-dichloro-3,5-dimethylphenoxy)ethyl]-1-methylpiperazin-1-ium-1-yl}methyl hydrogen phosphate;

{4-[2-(4-{4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-3,5-dimethylphenoxy)ethyl]-1-methylpiperazin-1-ium-1-yl}methyl hydrogen phosphate;

{[2-(4-{(5S$_a$)-4-[(1R)-1-carboxy-2-(2-{(2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl](dimethyl)ammonio}methyl hydrogen phosphate;

1-{4-[2-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}ethyl hydrogen phosphate;

1-{4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}ethyl hydrogen phosphate;

{1-[2-(4-{(5S$_a$)-4-(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-4-methylpiperazin-1-ium-1-yl}methyl hydrogen phosphate;

{1-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-4-methylpiperazin-1-ium-1-yl}methyl hydrogen phosphate;

{4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl sulfate;

1-[(acetyloxy)methyl]-4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium;

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-{[(ethoxycarbonyl)oxy]methyl}-1-methylpiperazin-1-ium;

4-[2-{4-(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-{[(diethylcarbamoyl)oxy]methyl)-1-methylpiperazin-1-ium;

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-[(glycyloxy)methyl]-1-methylpiperazin-1-ium;

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl)-2-chloro-3-methylphenoxy)ethyl]-1-{1-[(diethylcarbamoyl)oxy]ethyl}-1-methylpiperazin-1-ium;

4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methyl-1-[(5-methyl-2-oxo-1,3-dioxol-4-yl)methyl]piperazin-1-ium;

4-[2-4-{(5S$_a$)-4-((1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methyl-1-[(L-valyloxy)methyl]piperazin-1-ium;

4-[2-(4-{(5S$_a$)-4-[(1R)-1-carboxy-2-(2-{[2-(2-methoxyphenyl)pyrimidin-yl]methoxy}phenyl)ethoxy]-6-(4-fluorophenyl)thieno[2,3-d]pyrimidin-5-yl}-2-chloro-3-methylphenoxy)ethyl]-1-{([(2,2-dimethylpropanoyl)oxy]methyl}-1-methylpiperazin-1-ium;

1-[(acetyloxy)methyl]-4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium;

4-[2-(3-bromo-4-{(5S$_a$)-4-(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-{[(ethoxycarbonyl)oxy]methyl}-1-methylpiperazin-1-ium;

4-[2-(3-bromo-4-{(5S$_a$)-4-[(1R)-1-carboxy-2-(2-([2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-{[(diethylcarbamoyl)oxy]methyl}-1-methylpiperazin-1-ium;

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-[(glycyloxy)methyl]-1-methylpiperazin-1-ium;

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-{1-[(diethylcarbamoyl)oxy]ethyl}-1-methylpiperazin-1-ium;

4-[2-(3-bromo-4-{(5S$_a$)-(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methyl-1-[(5-methyl-2-oxo-1,3-dioxol-4-yl)methyl]piperazin-1-ium;

4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methyl-1-[(L-valyloxy)methyl]piperazin-1-ium; and 4-[2-(3-bromo-4-{(5S$_a$)-4-[(1R)-1-carboxy-2-(2-([2-(2-methoxyphenyl)pyrimidin-4-yl]methoxy}phenyl)

ethoxy]-6-(4-fluorophenyl)thieno[2,3-d]pyrimidin-5-yl)}-2-chlorophenoxy)ethyl]-1-([(2,2-dimethylpropanoyl)oxy]methyl}-1-methylpiperazin-1-ium.

14. The compound according to claim 1, which is {4-[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl]-1-methylpiperazin-1-ium-1-yl}methyl hydrogen phosphate.

15. The compound according to claim 1, which is {4-[2-(3-bromo-4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chlorophenoxy)ethyl]-1-methylpiperazin-1-ium-1-yl}methyl hydrogen phosphate.

16. The compound according to claim 1, which is {[2-(4-{(5S$_a$)-4-[(1R)-1-carboxy-2-(2-{[2-(2-methoxyphenyl)pyrimidin-4-yl]methoxy}phenyl)ethoxy]-6-(4-fluorophenyl)thieno[2,3-d]pyrimidin-5-yl}-2-chloro-3-methylphenoxy)ethyl](dimethyl)ammonio}methyl hydrogen phosphate.

17. A pharmaceutical composition comprising the compound according to claim 1, or an addition salt thereof with a pharmaceutically acceptable acid or base, in combination with one or more pharmaceutically acceptable excipients.

18. A method of treating a condition requiring a pro-apoptotic agent in a subject in need thereof, comprising administration of an effective amount of the compound according to claim 1, alone or in combination with one or more pharmaceutically acceptable excipients.

19. The method according to claim 18, wherein the condition is selected from cancer, auto-immune diseases and immune system diseases.

20. The method according to claim 19, wherein the condition is selected from cancers of the bladder, brain, breast and uterus, chronic lymphoid leukaemias, cancer of the colon, œsophagus and liver, lymphoblastic leukaemias, acute myeloid leukaemias, lymphomas, melanomas, malignant haemopathies, myelomas, ovarian cancer, non-small-cell lung cancer, prostate cancer, pancreatic cancer and small-cell lung cancer.

21. A combination of the compound according to claim 1, with an anti-cancer agent selected from genotoxic agents, mitotic poisons, anti-metabolites, proteasome inhibitors, kinase inhibitors and antibodies.

22. A pharmaceutical composition comprising the combination according to claim 21 in combination with one or more pharmaceutically acceptable excipients.

23. A method of treating cancer in a subject in need thereof, comprising administration of an effective amount of the combination according to claim 21, alone or in combination with one or more pharmaceutically acceptable excipients.

24. A method of treating cancer requiring radiotherapy in a subject in need thereof, comprising administration of an effective amount of the compound according to claim 3, alone or in combination with one or more pharmaceutically acceptable excipients.

* * * * *

UNITED STATES PATENT AND TRADEMARK OFFICE
CERTIFICATE OF CORRECTION

PATENT NO. : 10,457,689 B2  
APPLICATION NO. : 16/069891  
DATED : October 29, 2019  
INVENTOR(S) : Attila Paczal et al.

Page 1 of 1

It is certified that error appears in the above-identified patent and that said Letters Patent is hereby corrected as shown below:

Column 51, Line 7: "OR," should read -- $OR_9$, --.

Column 54, Line 27: "pyrimidin-yl" should read -- pyrimidin-4-yl --.

Signed and Sealed this  
Seventeenth Day of December, 2019

Andrei Iancu  
*Director of the United States Patent and Trademark Office*